(12) United States Patent
Utermohlen et al.

(10) Patent No.: US 8,236,502 B2
(45) Date of Patent: **\*Aug. 7, 2012**

(54) OLIGONUCLEOTIDE SEQUENCE FORMULA FOR LABELING OLIGNUCLEOTIDE PROBES AND PROTEINS FOR IN-SITU ANALYSIS

(75) Inventors: Joseph G. Utermohlen, Tucson, AZ (US); John F. Connaughton, Laytonsville, MD (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/910,454

(22) Filed: Oct. 22, 2010

(65) Prior Publication Data

US 2011/0034682 A1 Feb. 10, 2011

Related U.S. Application Data

(62) Division of application No. 10/380,584, filed as application No. PCT/US01/28014 on Sep. 6, 2001, now Pat. No. 7,838,655.

(60) Provisional application No. 60/233,177, filed on Sep. 15, 2000.

(51) Int. Cl.
  *C12Q 1/68* (2006.01)
  *C07H 21/02* (2006.01)
(52) U.S. Cl. .................. 435/6.1; 536/24.1; 536/24.3
(58) Field of Classification Search .................. None
  See application file for complete search history.

(56) References Cited

U.S. PATENT DOCUMENTS

| | | | |
|---|---|---|---|
| 3,948,922 | A | 4/1976 | Lowe |
| 5,489,507 | A | 2/1996 | Chehab |
| 5,521,298 | A | 5/1996 | Bahl et al. |
| 5,541,308 | A | 7/1996 | Hogan et al. |
| 5,684,142 | A | 11/1997 | Mishra et al. |
| 5,789,161 | A | 8/1998 | Morrison et al. |
| 5,843,660 | A | 12/1998 | Schumm et al. |
| 5,871,917 | A | 2/1999 | Duffy |
| 7,838,655 | B2 * | 11/2010 | Utermohlen et al. ........ 536/24.3 |
| 2006/0283323 | A1 | 12/2006 | Fan et al. |
| 2007/0031851 | A1 | 2/2007 | Velculescu et al. |

OTHER PUBLICATIONS

Abbaszadegan et al., "Automated Detection of Prevalent Mutations in BRCA1 and BRCA2 Genes, Using a Fluorogenic PCR Allelic Discrimination Assay," *Genetic Testing*, vol. 1, No. 3, pp. 171-180, 1997/1998.
Daniel et al., "FastTag Nucleic Acid Labeling System: A Versatile Method for Incorporating Haptens, Fluorochromes and Affinity Ligands into DNA, RNA and Oligonucleotides," *Biotechniques*, vol. 24, pp. 484-489, 1998.
Dirks et al., "3'-End Fluorochromized and Haptenized Oligonucleotides as in Situ Hybridization Probes for Multiple, Simultaneous RNA Detection," *Experimental Cell Research*, vol. 194, pp. 310-315, 1991.
Dirks et al., "Methodologies for specific intron and exon RNA localization in cultured cells by haptenized and fluorochromized probes," *Journal of Cell Science*, vol. 104, pp. 1187-1197, 1993.
Iezzoni et al., "Colorimetric detection of herpes simplex virus by DNA in situ sandwich hybridization: a rapid, formamide-free, random oligomer-enhanced method," *Nucleic Acids Research*, vol. 20, No. 5, pp. 1149-1150, 1992.
Ofir et al., "The ftsZ gene as a tool for detection of Mycoplasma fermentans," *Molecular and Cellular Probes*, vol. 12, pp. 85-92, 1998.
Rudert et al., "Double-Labeled Fluorescent Probes for 5' Nuclease Assays: Purification and Performance Evaluation," *Biotechniques*, vol. 22, No. 6, pp. 1140-1145, 1997.
Sauvaigo et al., "Fast Solid Support Detection of PCR Amplified Viral DNA Sequences Using Radioiodinated or Hapten Labeled Primers," *Nucleic Acids Research*, vol. 18, No. 11, pp. 3175-3183, 1990.
Sumiyoshi et al., "Analysis of immunoglobulin light-chain mRNA in gastric malignant lymphoma using new highly sensitive in situ hybridization method," *Gastric Cancer*, vol. 2, pp. 8-13, 1999.
Wessendorf et al., "Which fluorophore is brightest? A comparison of the staining obtained using fluorescein, tetramethylrhodamine, lissamine rhodamine, Texas red, and cyanine 3.18," *Histochemistry*, vol. 98, p. 81-85, 1992.
Zhu et al., "Unique dicistronic operon (ptsI-crr) in Mycoplasma capricolum encoding enzyme I and the glucose-specific enzyme IIA of the phosphoenopyruvate: sugar phosphotransferase system: Cloning, sequencing, promoter analysis, and protein characterization," *Protein Science*, vol. 3, pp. 2115-2128, 1994.
Database EMBL, "Soares Mouse Embryo," Accession No. W54035, 2 pages, 1996.
GENBANK Accession No. W54035 (Jun. 3, 1996, NCBI website).
GENBANK Accession No. X84406 (Feb. 9, 1995, NCBI website).
GENBANK Accession No. X72444 (Jan. 31, 1994, NCBI website).
GENBANK Accession No. U97015 (Apr. 16, 1997, NCBI Website).
International Search Report, PCT/US01/28014, completed on Jan. 10, 2003.
International Search Report, PCT/US01/28014, completed on Feb. 4, 2003.

\* cited by examiner

*Primary Examiner* — Katherine Salmon
(74) *Attorney, Agent, or Firm* — Klarquist Sparkman, LLP.

(57) ABSTRACT

The present invention provides oligonucleotide probes and oligonucleotide probe collections and protein labeling for detecting or localizing a plurality nucleic acid target genes or antigens within a cell or tissue sample. Specifically, the invention provides collections of oligonucleotide probes for use in in situ hybridization analyses in which each probe has a label-domain with the sequence formulas of $(CTATTTT)_n CT$, $(AAAATAG)_n$, or $(TTTTATC)_n$, or $(GATAAAA)_n$, in which all cases "n" would equal 1 or greater. The present invention provides collections or "cocktails" of oligonucleotide probes for detecting or localizing specific nucleic acid target genes within a cell or tissue sample. The cocktails are useful for detecting the following: the Kappa gene (SEQ ID NOS: 1-16 inclusive); the Lambda gene (SEQ ID NOS: 17 through 29 inclusive); the CMV (cytomegalovirus) gene (SEQ ID NOS: 30 through 50 inclusive); EBER (Epstein-Barr early RNA) gene (SEQ ID NOS: 51-54 inclusive); Alu (SEQ ID NOS: 55-56); PolyA (SEQ ID NO: 57); and the detection tail (SEQ ID NO: 58).

6 Claims, 21 Drawing Sheets

Oligonucleotide Probe Design

Common Signal Detection Region    Unique Target Detection Region

5'-  -3'

Alu301 5'-CTATTTTCTATTTTCTATTTTCT-CGAGGCGGGATCACCTGAGGTC-3'

Alu302 5'-CTATTTTCTATTTTCTATTTTCT-CGGGAGGCGGAGGTTGCAGTGAGCC-3'

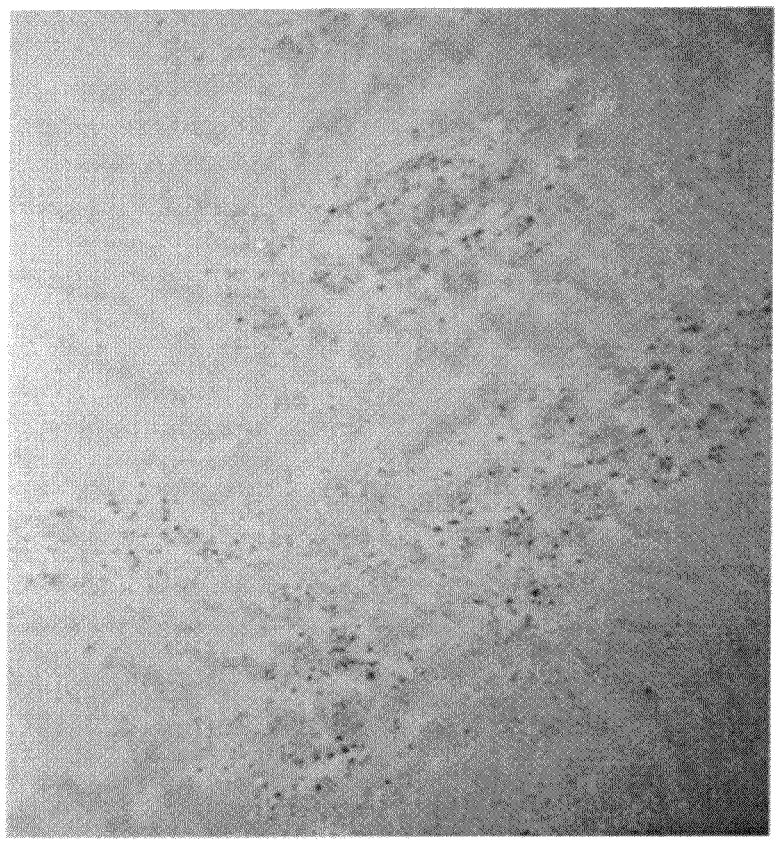
FIG. 13B PLUS RNase
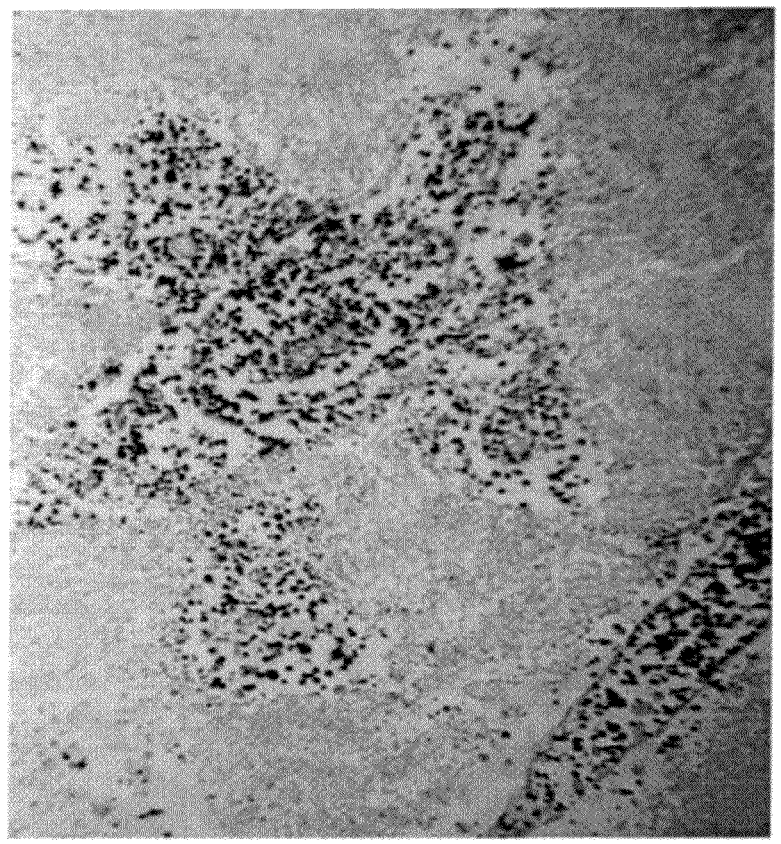
FIG. 13A MINUS RNase

SEQUENCE LISTING

<160> NUMBER OF SEQ ID NOS: 126

<210> SEQ ID NO 1
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 1
ctattttcta ttttctattt tctattttct ccagagtagc aggagcccca ggagctgagc    60

<210> SEQ ID NO 2
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 2
ctattttcta ttttctattt tctattttct ggatggagac tgggtcaact ggatgtcaca    60

<210> SEQ ID NO 3
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 3
ctattttcta ttttctattt tctattttct gcaagcgatg gtgactctgt ctcctacagc    60

<210> SEQ ID NO 4
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 4
ctattttcta ttttctattt tctattttct tctgtcccag atccactgcc actgaacctt    60

<210> SEQ ID NO 5
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 5
ctattttcta ttttctattt tctattttct gcagccacag ttcgcttcat ctgcaccttg    60

<210> SEQ ID NO 6
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 6
ctattttcta ttttctattt tctattttct tttcaactgc tcatcagatg gcgggaagat    60

<210> SEQ ID NO 7
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 7
ctattttcta ttttctattt tctattttct aagttattca gcaggcacac aacagaggca    60

<210> SEQ ID NO 8
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 8
ctattttcta ttttctattt tctattttct ggcgttatcc accttccact gtactttggc    60

<210> SEQ ID NO 9
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 9
ctattttcta ttttctattt tctattttct taggtgctgt ccttgctgtc ctgctctgtg    60

<210> SEQ ID NO 10
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 10
ctattttcta ttttctattt tctattttct gtagtctgct ttgctcagcg tcagggtgct    60

<210> SEQ ID NO 11
<211> LENGTH: 60
<212> TYPE: DNA
<213> ORGANISM: Artificial Sequence

```
<220> FEATURE:
<223> OTHER INFORMATION: oligonucleotide probe

<400> SEQUENCE: 11
ctattttcta ttttctattt tctattttct gatgggtgac ttcgcaggcg tagactttgt    60

<210> SEQ ID NO 12
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 12
ctattttcta ttttctattt tctattttct ctctcccctg ttgaagctct ttgtgacggg    60

<210> SEQ ID NO 13
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 13
ctattttcta ttttctattt tctattttct tggaactgag gagcaggtgg gggcacttct    60

<210> SEQ ID NO 14
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 14
ctattttcta ttttctattt tctattttct gaaaaagggt cagaggccaa aggatgggag    60

<210> SEQ ID NO 15
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 15
ctattttcta ttttctattt tctattttct agatgagctg gaggaccgca atagggtag    60

<210> SEQ ID NO 16
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 16
ctattttcta ttttctattt tctattttct gcataattaa agccaaggag gaggagggg    60

<210> SEQ ID NO 17
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 17
ctattttcta ttttctattt tctattttct cctgagtgag gagggtgagg agcagcagag    60
```

```
<210> SEQ ID NO 18
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 18
ctattttcta ttttctattt tctattttct agacccagac acggaggcag gctgagtcag      60

<210> SEQ ID NO 19
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 19
ctattttcta ttttctattt tctattttct tgttggttcc agtgcaggag atggtgatcg      60

<210> SEQ ID NO 20
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 20
ctattttcta ttttctattt tctattttct taaatcatga ttttgggggc tttgcctggg      60

<210> SEQ ID NO 21
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 21
ctattttcta ttttctattt tctattttct tgttgccaga cttggagcca gagaagcgat      60

<210> SEQ ID NO 22
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 22
ctattttcta ttttctattt tctattttct aataatcagc ctcgtcctca gcctggagcc      60

<210> SEQ ID NO 23
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 23
ctattttcta ttttctattt tctattttct ggtccctccg ccgaaaacca cagtgtaact      60

<210> SEQ ID NO 24
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 24
```
ctattttcta ttttctattt tctattttct ttatgagaca caccagtgtg gccttgttgg    60

<210> SEQ ID NO 25
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 25
ctattttcta ttttctattt tctattttct ctgctcaggc gtcaggctca gatagctgct    60

<210> SEQ ID NO 26
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 26
ctattttcta ttttctattt tctattttct atgcgtgacc tggcagctgt agcttctgtg    60

<210> SEQ ID NO 27
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 27
ctattttcta ttttctattt tctattttct attctgtagg ggccactgtc ttctccacgg    60

<210> SEQ ID NO 28
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 28
ctattttcta ttttctattt tctattttct cctcccctgg gatcctgcag ctctagtctc    60

<210> SEQ ID NO 29
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 29
ctattttcta ttttctattt tctattttct tgagggttta ttgagtgcag ggagaagggc    60

<210> SEQ ID NO 30
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 30
ctattttcta ttttctattt tctattttct ggaggtcaaa acagcgtgga tggcg    55

<210> SEQ ID NO 31
<211> LENGTH: 55
<212> TYPE: DNA
<213> ORGANISM: Artificial Sequence

```
<220> FEATURE:
<223> OTHER INFORMATION: oligonucleotide probe

<400> SEQUENCE: 31
ctattttcta ttttctattt tctattttct gaggctggat cggtcccggt gtctt      55

<210> SEQ ID NO 32
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 32
ctattttcta ttttctattt tctattttct aatccgcgtt ccaatgcacc gttcc      55

<210> SEQ ID NO 33
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 33
ctattttcta ttttctattt tctattttct taaaaactgc gggcactggg gacgg      55

<210> SEQ ID NO 34
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 34
ctattttcta ttttctattt tctattttct acccgagatt cgcgtggaga tccca      55

<210> SEQ ID NO 35
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 35
ctattttcta ttttctattt tctattttct gagcaaggag ctgccgagcg accat      55

<210> SEQ ID NO 36
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 36
ctattttcta ttttctattt tctattttct acactggtgg tggtgggcat cgtgc      55

<210> SEQ ID NO 37
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 37
ctattttcta ttttctattt tctattttct ttccaaatgc gtcagcggtg caagc      55
```

```
<210> SEQ ID NO 38
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 38
ctattttcta ttttctattt tctattttct agctgcctgc atcttcttct gccgc        55

<210> SEQ ID NO 39
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 39
ctattttcta ttttctattt tctattttct ccctccaccg ttaacagcac cgcaa        55

<210> SEQ ID NO 40
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 40
ctattttcta ttttctattt tctattttct ttggtcacgg gtgtctcggg cctaa        55

<210> SEQ ID NO 41
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 41
ctattttcta ttttctattt tctattttct tcggccaact ctggaaacag cgggt        55

<210> SEQ ID NO 42
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 42
ctattttcta ttttctattt tctattttct tcggggttct cgttgcaatc ctcgg        55

<210> SEQ ID NO 43
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 43
ctattttcta ttttctattt tctattttct atctcgatgc cccgctcaca tgcaa        55

<210> SEQ ID NO 44
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 44
```

```
ctattttcta ttttctattt tctattttct tgccgcacca tgtccactcg aacct        55

<210> SEQ ID NO 45
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 45
ctattttcta ttttctattt tctattttct gttagcggcg cccttgctca catca        55

<210> SEQ ID NO 46
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 46
ctattttcta ttttctattt tctattttct tgcagatctc ctcaatgcgg cgctt        55

<210> SEQ ID NO 47
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 47
ctattttcta ttttctattt tctattttct tctcagagga tcggcccccca gaatg       55

<210> SEQ ID NO 48
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 48
ctattttcta ttttctattt tctattttct cctcatctga ctcctcggcg atggc        55

<210> SEQ ID NO 49
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 49
ctattttcta ttttctattt tctattttct cgggtacagg ggactctggg ggtga        55

<210> SEQ ID NO 50
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 50
ctattttcta ttttctattt tctattttct gggtgggtgc tcttgcctcc agagg        55

<210> SEQ ID NO 51
<211> LENGTH: 55
<212> TYPE: DNA
<213> ORGANISM: Artificial Sequence
```

```
<220> FEATURE:
<223> OTHER INFORMATION: oligonucleotide probe

<400> SEQUENCE: 51
ctattttcta ttttctattt tctattttct gacctcgggt cggtagcacc gcact            55

<210> SEQ ID NO 52
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 52
ctattttcta ttttctattt tctattttct ggaagcctct cttctcctcc cccgg            55

<210> SEQ ID NO 53
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 53
ctattttcta ttttctattt tctattttct ccacagacac cgtcctcacc acccg            55

<210> SEQ ID NO 54
<211> LENGTH: 56
<212> TYPE: DNA
<213> ORGANISM: Artificial Sequence
<220> FEATURE:
<223> OTHER INFORMATION: oligonucleotide probe

<400> SEQUENCE: 54
ctattttcta ttttctattt tctattttct ggctacagcc acacacgtct cctccc           56

<210> SEQ ID NO 55
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 55
ctattttcta ttttctattt tctattttct cgaggcgggc ggatcacctg aggtc            55

<210> SEQ ID NO 56
<211> LENGTH: 55
<212> TYPE: DNA
<213> ORGANISM: Artificial Sequence
<220> FEATURE:
<223> OTHER INFORMATION: oligonucleotide probe

<400> SEQUENCE: 56
ctattttcta ttttctattt tctattttct cgggaggcgg aggttgcagt gagcc            55

<210> SEQ ID NO 57
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 57
ctattttcta ttttctattt tctattttct tttttttttt tttttttttt tttttttttt       60
```

<210> SEQ ID NO 58
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 58
ctattttcta ttttctattt tctattttct                               30

<210> SEQ ID NO 59
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 59
ccagagtagc aggagcccca ggagctgagc                               30

<210> SEQ ID NO 60
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 60
ggatggagac tgggtcaact ggatgtcaca                               30

<210> SEQ ID NO 61
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 61
gcaagcgatg gtgactctgt ctcctacagc                               30

<210> SEQ ID NO 62
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 62
tctgtcccag atccactgcc actgaacctt                               30

<210> SEQ ID NO 63
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 63
gcagccacag ttcgcttcat ctgcaccttg                               30

<210> SEQ ID NO 64
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 64

```
tttcaactgc tcatcagatg gcgggaagat                                       30

<210> SEQ ID NO 65
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 65
aagttattca gcaggcacac aacagaggca                                       30

<210> SEQ ID NO 66
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 66
ggcgttatcc accttccact gtactttggc                                       30

<210> SEQ ID NO 67
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 67
taggtgctgt ccttgctgtc ctgctctgtg                                       30

<210> SEQ ID NO 68
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 68
gtagtctgct ttgctcagcg tcagggtgct                                       30

<210> SEQ ID NO 69
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 69
gatgggtgac ttcgcaggcg tagactttgt                                       30

<210> SEQ ID NO 70
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 70
ctctcccctg ttgaagctct ttgtgacggg                                       30

<210> SEQ ID NO 71
<211> LENGTH: 30
<212> TYPE: DNA
<213> ORGANISM: Artificial Sequence
```

-continued

```
<220> FEATURE:
<223> OTHER INFORMATION: oligonucleotide probe

<400> SEQUENCE: 71
tggaactgag gagcaggtgg gggcacttct                                           30

<210> SEQ ID NO 72
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 72
gaaaaagggt cagaggccaa aggatgggag                                           30

<210> SEQ ID NO 73
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 73
agatgagctg gaggaccgca atagggtag                                            30

<210> SEQ ID NO 74
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 74
gcataattaa agccaaggag gaggaggggg                                           30

<210> SEQ ID NO 75
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 75
cctgagtgag gagggtgagg agcagcagag                                           30

<210> SEQ ID NO 76
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 76
agacccagac acggaggcag gctgagtcag                                           30

<210> SEQ ID NO 77
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 77
tgttggttcc agtgcaggag atggtgatcg                                           30
```

```
<210> SEQ ID NO 78
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 78
taaatcatga ttttgggggc tttgcctggg                                    30

<210> SEQ ID NO 79
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 79
tgttgccaga cttggagcca gagaagcgat                                    30

<210> SEQ ID NO 80
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 80
aataatcagc ctcgtcctca gcctggagcc                                    30

<210> SEQ ID NO 81
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 81
ggtccctccg ccgaaaacca cagtgtaact                                    30

<210> SEQ ID NO 82
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 82
ttatgagaca caccagtgtg gccttgttgg                                    30

<210> SEQ ID NO 83
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 83
ctgctcaggc gtcaggctca gatagctgct                                    30

<210> SEQ ID NO 84
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 84
```

```
atgcgtgacc tggcagctgt agcttctgtg                                          30

<210> SEQ ID NO 85
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 85
attctgtagg ggccactgtc ttctccacgg                                          30

<210> SEQ ID NO 86
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 86
cctcccctgg gatcctgcag ctctagtctc                                          30

<210> SEQ ID NO 87
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 87
tgagggttta ttgagtgcag ggagaagggc                                          30

<210> SEQ ID NO 88
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 88
ggaggtcaaa acagcgtgga tggcg                                               25

<210> SEQ ID NO 89
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 89
gaggctggat cggtcccggt gtctt                                               25

<210> SEQ ID NO 90
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 90
aatccgcgtt ccaatgcacc gttcc                                               25

<210> SEQ ID NO 91
<211> LENGTH: 25
<212> TYPE: DNA
<213> ORGANISM: Artificial Sequence
```

```
<220> FEATURE:
<223> OTHER INFORMATION: oligonucleotide probe

<400> SEQUENCE: 91
taaaaactgc gggcactggg gacgg                                        25

<210> SEQ ID NO 92
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 92
acccgagatt cgcgtggaga tccca                                        25

<210> SEQ ID NO 93
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 93
gagcaaggag ctgccgagcg accat                                        25

<210> SEQ ID NO 94
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 94
acactggtgg tggtgggcat cgtgc                                        25

<210> SEQ ID NO 95
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 95
ttccaaatgc gtcagcggtg caagc                                        25

<210> SEQ ID NO 96
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 96
agctgcctgc atcttcttct gccgc                                        25

<210> SEQ ID NO 97
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 97
ccctccaccg ttaacagcac cgcaa                                        25
```

```
<210> SEQ ID NO 98
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 98
ttggtcacgg gtgtctcggg cctaa                                        25

<210> SEQ ID NO 99
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 99
tcggccaact ctggaaacag cgggt                                        25

<210> SEQ ID NO 100
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 100
tcggggttct cgttgcaatc ctcgg                                        25

<210> SEQ ID NO 101
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 101
atctcgatgc cccgctcaca tgcaa                                        25

<210> SEQ ID NO 102
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 102
tgccgcacca tgtccactcg aacct                                        25

<210> SEQ ID NO 103
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 103
gttagcggcg cccttgctca catca                                        25

<210> SEQ ID NO 104
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 104
```

```
tgcagatctc ctcaatgcgg cgctt                                              25

<210> SEQ ID NO 105
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 105
tctcagagga tcggccccca gaatg                                              25

<210> SEQ ID NO 106
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 106
cctcatctga ctcctcggcg atggc                                              25

<210> SEQ ID NO 107
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 107
cgggtacagg ggactctggg ggtga                                              25

<210> SEQ ID NO 108
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 108
gggtgggtgc tcttgcctcc agagg                                              25

<210> SEQ ID NO 109
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 109
gacctcgggt cggtagcacc gcact                                              25

<210> SEQ ID NO 110
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 110
ggaagcctct cttctcctcc cccgg                                              25

<210> SEQ ID NO 111
<211> LENGTH: 25
<212> TYPE: DNA
<213> ORGANISM: Artificial Sequence
```

```
<220> FEATURE:
<223> OTHER INFORMATION: oligonucleotide probe

<400> SEQUENCE: 111
ccacagacac cgtcctcacc acccg                                           25

<210> SEQ ID NO 112
<211> LENGTH: 26
<212> TYPE: DNA
<213> ORGANISM: Artificial Sequence
<220> FEATURE:
<223> OTHER INFORMATION: oligonucleotide probe

<400> SEQUENCE: 112
ggctacagcc acacacgtct cctccc                                          26

<210> SEQ ID NO 113
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 113
cgaggcgggc ggatcacctg aggtc                                           25

<210> SEQ ID NO 114
<211> LENGTH: 25
<212> TYPE: DNA
<213> ORGANISM: Artificial Sequence
<220> FEATURE:
<223> OTHER INFORMATION: oligonucleotide probe

<400> SEQUENCE: 114
cgggaggcgg aggttgcagt gagcc                                           25

<210> SEQ ID NO 115
<211> LENGTH: 30
<212> TYPE: DNA
<213> ORGANISM: Artificial Sequence
<220> FEATURE:
<223> OTHER INFORMATION: oligonucleotide probe

<400> SEQUENCE: 115
tttttttttt tttttttttt tttttttttt                                      30

<210> SEQ ID NO 116
<211> LENGTH: 46
<212> TYPE: DNA
<213> ORGANISM: Artificial Sequence
<220> FEATURE:
<223> OTHER INFORMATION: oligonucleotide probe

<400> SEQUENCE: 116
ctattttcct atttttcttt tcgaggcggg cggatcacct gaggtc                    46

<210> SEQ ID NO 117
<211> LENGTH: 46
<212> TYPE: DNA
<213> ORGANISM: Artificial Sequence
<220> FEATURE:
<223> OTHER INFORMATION: oligonucleotide probe

<400> SEQUENCE: 117
ctattttcct atttttcttt tcgggaggcg gaggttgcag tgagcc                    46
```

```
<210> SEQ ID NO 118
<211> LENGTH: 57
<212> TYPE: DNA
<213> ORGANISM: Artificial Sequence
<220> FEATURE:
<223> OTHER INFORMATION: oligonucleotide probe

<400> SEQUENCE: 118
ctattttata ctttatattt catattttat ctcgggaggc ggaggttgca gtgagcc        57

<210> SEQ ID NO 119
<211> LENGTH: 60
<212> TYPE: DNA
<213> ORGANISM: Artificial Sequence
<220> FEATURE:
<223> OTHER INFORMATION: oligonucleotide probe

<400> SEQUENCE: 119
ctattttata tttatatttc tcgggaggcg gaggttgcag tgagccacta ttttatactt     60

<210> SEQ ID NO 120
<211> LENGTH: 61
<212> TYPE: DNA
<213> ORGANISM: Artificial Sequence
<220> FEATURE:
<223> OTHER INFORMATION: oligonucleotide probe

<400> SEQUENCE: 120
ctattttata ctttatattt ctgacctcgg gtcggtagca ccgcactact attttatact     60
t                                                                    61

<210> SEQ ID NO 121
<211> LENGTH: 49
<212> TYPE: DNA
<213> ORGANISM: Artificial Sequence
<220> FEATURE:
<223> OTHER INFORMATION: oligonucleotide probe

<400> SEQUENCE: 121
ctatttttct tcgaggcggg cggatcacct gaggtcttct ttttatctt                 49

<210> SEQ ID NO 122
<211> LENGTH: 61
<212> TYPE: DNA
<213> ORGANISM: Artificial Sequence
<220> FEATURE:
<223> OTHER INFORMATION: oligonucleotide probe

<400> SEQUENCE: 122
ctattttata ctttatattt ctcgaggcgg gcggatcacc tgaggtcact attttatact     60
t                                                                    61

<210> SEQ ID NO 123
<211> LENGTH: 21
<212> TYPE: DNA
<213> ORGANISM: Artificial Sequence
<220> FEATURE:
<223> OTHER INFORMATION: oligonucleotide probe

<400> SEQUENCE: 123
ctatttttct attttttcttt t                                              21

<210> SEQ ID NO 124
<211> LENGTH: 32
<212> TYPE: DNA
<213> ORGANISM: Artificial Sequence
```

```
<220> FEATURE:
<223> OTHER INFORMATION: oligonucleotide probe

<400> SEQUENCE: 124
ctattttata ctttatattt catattttat ct                                  32

<210> SEQ ID NO 125
<211> LENGTH: 61
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (23)..(47)
<223> OTHER INFORMATION: "n" can be a, g, c, or t

<400> SEQUENCE: 125
ctattttata ctttatattt ctnnnnnnnn nnnnnnnnnn nnnnnnnact attttatact    60
t                                                                    61

<210> SEQ ID NO 126
<211> LENGTH: 49
<212> TYPE: DNA
<213> ORGANISM: Artificial Sequence
<220> FEATURE:
<223> OTHER INFORMATION: oligonucleotide probe
<220> FEATURE:
<221> NAME/KEY: misc_feature
<222> LOCATION: (12)..(36)
<223> OTHER INFORMATION: "n" can be a, g, c, or t

<400> SEQUENCE: 126
ctatttttct tnnnnnnnnn nnnnnnnnnn nnnnnnttct ttttatctt                49
```

US 8,236,502 B2

OLIGONUCLEOTIDE SEQUENCE FORMULA FOR LABELING OLIGNUCLEOTIDE PROBES AND PROTEINS FOR IN-SITU ANALYSIS

CROSS-REFERENCE TO RELATED APPLICATIONS

This is a divisional of U.S. patent application Ser. No. 10/380,584, which was filed Jul. 21, 2003, now U.S. Pat. No. 7,838,655 and met the requirements under 35 U.S.C. §371 (c)(1), (c)(2), and (c)(4) on Jul. 21, 2003, which is the U.S. §371 National Phase application of PCT/US2001/28014, filed Sep. 6, 2001 (published in English under PCT Article 21(2)), which in turn claims the benefit of U.S. Provisional Patent Application No. 60/233,177, filed Sep. 15, 2000, all of which are incorporated by reference herein in their entirety.

BACKGROUND OF THE INVENTION

1. Field of the Invention

This invention relates to oligonucleotide probes and collections of oligonucleotide probes for detecting or localizing nucleic acid genes targets within a cell or tissue sample. In particular, the invention relates to collections of oligoprobes.

2. Background of the Invention

In situ analysis includes in situ hybridization and immunohistochemistry. In situ hybridization (ISH) employs labeled DNA or RNA probe molecules that are anti-sense to a target gene sequence or transcript to detect or localize targeted nucleic acid target genes within a cell or tissue sample. ISH has proven to be a useful tool in a number of biomedical fields, including developmental biology, cell biology, and molecular biology. ISH has been used, for example, to diagnose genetic disorders, map genes, study gene expression, and localize sites of target gene expression.

Typically, ISH is performed by exposing a cell or tissue sample immobilized on a glass slide to a labeled nucleic acid probe which is capable of specifically hybridizing to a given target gene in the cell or tissue sample (*In Situ Hybridization: Medical Applications* (G. R. Coulton and J. de Belleroche, eds., Kluwer Academic Publishers, 1992); *In Situ Hybridization: In Neurobiology; Advances in Methodology* (J. H. Eberwine, K. L. Valentino, and J. D. Barchas, eds., Oxford University Press, 1994); *In Situ Hybridization: A Practical Approach* (D. G. Wilkinson, ed., Oxford University Press, 1992)). The hybridization of labeled probe molecules to nucleic acids in the cell or tissue sample can then be detected using, for example, radioactive-based direct detection methods, fluorescence-based direct detection methods, or indirect detection methods based on the binding of a fluorescence-labeled protein binding to a hapten such as BrdU, digoxigenin-labeled or biotin-labeled nucleotides incorporated into probes. Hapten-based methods have been further extended to include those molecules to be bonded by binding protein-enzyme conjugates such as antibody-enzyme-conjugates and colorimetric based detection chemistry. In addition, several target genes can be simultaneously analyzed by exposing a cell or tissue sample to a plurality of nucleic acid probes that have been labeled with a plurality of different nucleic acid tags. For example, a plurality of nucleic acid probes can be labeled with a plurality of fluorescent compounds having different emission wavelengths, thereby permitting simultaneous multicolored analysis to be performed in a single step on a single target cell or tissue sample.

A significant problem associated with incorporation of labeled nucleotides into oligonucleotide probes is that the conjugation moieties that are attached to the nucleotide usually interfere with the formation of Watson-Crick base pairing, thus negatively affecting the hybridization of the probe to its target. The has been seen with use of label attached via N4-substituted cytosine nucleotides, because of steric hindrance and the expected shift to the less reactive state of a secondary amine (as seen with N4 labeled cytosine), as compared to the natural G-C bond formed with an unsubstituted cytosine (a primary amine). Any small change or interference with G-C bonding in a small oligonucleotide (25 to 50 bases) can reduce the ability of these oligos to hybridize with the intended targeted sequence.

There remains a need in the art to develop suitable probes designs for incorporating labeled nucleotides in oligonucleotide probes. We demonstrate that a few artificial sequences are viable alternatives for probe labeling and also work both singly and in complex oligonucleotide probe mixtures for detecting or localizing nucleic acid target genes within a cell or tissue sample. The development of such generic sequences and labeling strategy for probe collections has wide application in the medical, genetic, and molecular biological arts.

This interference due to labeling chemistry and hybridization stringency and kinetics is solved herein by designing the oligo to have at least two distinct functional domains, one domain or sequence to be gene specific and involved in the base pair formation, and the second domain to be an artificial, non-specific sequence (in reference to the sample's genome) comprised of spacing nucleotides and the labeled nucleotide. These elements are positioned so that these label-nucleotides are more accessible as haptens for binding proteins (immunoglobulin or avidin(s)) and thus do not interfere with Watson-Crick base pairing in the gene-specific domain.

SUMMARY OF THE INVENTION

The present invention provides a novel strategy to incorporate label into oligonucleotide probes and labeled oligonucleotide probe collections for detecting or localizing nucleic acid target genes within a cell or tissue sample. In particular, the invention relates to non-gene-specific sequences using sequence formulas for making repetitive polymers of such sequences which can be incorporated into collections of oligonucleotide probes for use in in situ hybridization analyses. In addition, using labeled synthetic oligonucleotide polymers, based on sequence formulas, when conjugated to binding proteins, i.e. immunoglobulins, is a very effective and controlled process for labeling such proteins used in immunohistochemical analysis. The present invention provides collections or "cocktails" of oligonucleotide probes for detecting or localizing specific nucleic acid target genes within a cell or tissue sample. The cocktails are useful for detecting the following: the Kappa gene (SEQ ID NOS: 1-16 inclusive); the Lambda gene (SEQ ID NOS: 17-19); the CMV (cytomegalovirus) gene (SEQ ID NOS: 30-50 inclusive); EBER (Epstein-Barr early RNA) gene (SEQ ID NOS: 51-54 inclusive); Alu (SEQ ID NOS: 55-56); PolyA (SEQ ID NO: 57); and the detection tail (SEQ ID NO: 58).

The invention is directed to an oligonucleotide label-domain comprising the sequence $(CTATTTT)_n$ and its complement $(AAAATAG)_n$ wherein "n" is at least 1.

The invention is also directed to an oligonucleotide probe having at least two distinct functional domains, a first domain comprising the label-domain of claim 2, and a second domain comprising a gene-specific target sequence.

The invention is also directed to a probeset for detecting Kappa immunoglobulin light chain mRNA or corresponding hetereonuclear RNA wherein the probes are selected from the group consisting essentially of SEQ ID NOS: 1 through 16, inclusive.

The invention is also directed to a probeset for detecting Lambda immunoglobulin light chain mRNA or corresponding hetereonuclear RNA wherein the probes are selected from the group consisting essentially of SEQ ID NOS: 17-29.

The invention is also directed to a probeset for detecting cytomegalovirus (CMV) immediate early RNA and/or corresponding mRNA wherein the probes are selected from the group consisting essentially of SEQ ID NOS: 30 through 50.

The invention is also directed to a probeset for detecting Epstein Barr virus (EBV) early RNA, RNA 1 and RNA 2, (EBER) wherein the probes are selected from the group consisting essentially of SEQ ID NOS: 51 through 54.

The invention is also directed to a probeset for detecting Human Alu repetitive satellite genomic DNA sequences wherein the probes are selected from the group consisting essentially of SEQ ID NOS: 55 and 56.

Specific preferred embodiments of the present invention will become evident from the following more detailed description of certain preferred embodiments and the claims.

BRIEF DESCRIPTION OF THE DRAWINGS

FIGS. 13A-13B illustrate the results obtained for ISH analysis of human spleen tissue using a probe collection consisting of probes possessing target gene-specific domains corresponding to EBV EBER 1 and 2 nuclear RNA (SEQ ID NO:51 through SEQ ID NO:54), wherein the tissue sample was not treated with ribonuclease A prior to in situ hybridization (A), or was treated with ribonuclease A prior to in situ hybridization (B). The decrease in detectable signal in (B) indicates that this probe specifically hybridizes to human EBER 1 and EBER 2 nuclear RNA.

DETAILED DESCRIPTION OF THE PREFERRED EMBODIMENTS

Figure 1:
FIG. 1 illustrates a generic probe structure of the two-domain probe design. This is the oligonucleotide design used for the probes in the gene specific cocktails described in the following examples. Each probe is composed of two domains: a 5' labeling domain and a 3' target gene target gene-specific domain. The labeling domain consists of this specific sequence (CTATTTT)n, wherein each cytosine may be labeled with a fluorophore or a cytosine-hapten conjugate, the hapten being fluorescein in this embodiment. This illustration specifically shows nucleic acid sequences for the 301 (SEQ ID NO: 55) and 302 (SEQ ID NO: 56) probes, each of which possesses target gene gene-specific domains corresponding to human repetitive Alu sequences and labeling domains having a fluorescein hapten.

The present invention provides oligonucleotide probes and oligonucleotide probe collections for detecting or localizing nucleic acid target genes within a cell or tissue sample. In particular, the invention relates to collections of oligonucleotide probes for use in in situ hybridization analyses.

More specifically, this invention relates to the use of specific sequence formulas for nucleotide polymers or label-domains to attach a detectable moiety (a label) to oligonucleotide probes or proteins. The specific utility of these sequences or derivatives thereof, is the inert or non-reactive characteristic that does not hybridize to human DNA or RNA at a detectable level under standard stringency of hybridization conditions. These label-domains or polymers were demonstrated to be useful generic sequences for incorporation into oligonucleotide probes for detecting gene-specific sequences within cells or tissue samples in in situ hybridization analyses. Additionally, this inert set of sequences are useful for attaching a label to immunoglobulins or other proteins for detecting haptens and antigens in immunohistochemical analyses.

As used herein, the terms "probe" or "oligonucleotide probe" refers to a nucleic acid molecule used to detect a complementary nucleic acid target gene.

As used herein, the term "hybridization" refers to the process whereby complementary nucleic acid sequences join to form a double-stranded nucleic acid molecule. By labeling the target nucleic acid molecule with, for example, a radioactive or fluorescent tag, interactions between probe and target genes can be detected.

The oligonucleotide probes and oligonucleotide probes of the collections of the present invention are synthesized using conventional methods. See e.g., *Methods in Molecular Biology, Vol* 20: *Protocols for Oligonucleotides and Analogs* 165-89 (S. Agrawal, ed., 1993); *Oligonucleotides and Analogues: A Practical Approach* 87-108 (F. Eckstein, ed., 1991).

In a preferred embodiment of the present invention, oligonucleotide probes possess two distinct domains: a 5' (or labeling) domain and a 3' (or gene-specific target) domain (See FIG. 1A). In more preferred embodiments of the present invention, the oligonucleotide probe possesses a labeling domain which consists of the unique sequences $(CTATTTT)_n$ and/or $(CTATTTT)_n CT$. Other embodiments are also demonstrated herein, including a triple-domain embodiment having two terminal labeling domains, and a central gene-specific target domain. Specifically, SEQ ID NOS: 125-126 depict this labeling scheme. Yet a further preferred embodiment of a labeling domain is $TC(TTTTATC)_n$ or its complement. This sequence is predicted to be as unique as the $(CTATTTT)_n CT$ label-domain. The oligonucleotide probes of the present invention are labeled so that hybridization between said probes and target nucleic acids in a particular cell or tissue can be detected. Labels that are acceptable for use in in situ hybridization (ISH) analysis are known to those with skill in the art. Such labels permit interactions between probe and target genes to be detected using, for example, radioactive-based direct detection methods, fluorescence-based direct detection methods, digoxigenin-labeled or biotin-labeled probes coupled with fluorescence-based detection methods, or digoxigenin-labeled or biotin-labeled probes coupled with antibody-enzyme-based detection methods. In preferred embodiments of the present invention, oligonucleotide probes are labeled with fluorescein. In more preferred embodiments of the present invention, the oligonucleotide probe possesses a labeling domain which consists of the sequence $(CTATTTT)_n CT$, wherein the cytosine nucleotides may be labeled with a fluorophore for direct detection, or a hapten for indirect detection. In either, the fluorescein-cytosine nucleotide conjugate and the fluorescein molecule is linked at the N4 position of cytosine through an OBEA linkage (See Mishra et al., U.S. Pat. No. 5,684,142, which is incorporated herein by reference). In a preferred embodiment, the density of fluorophore attached to the label-domain is at least 7 mole percent, preferably at least 10 mole percent, and most preferably at least 16 mole percent, when measured against the label-domain solely. For example, if probe 401 is considered (a 2-domain probe) it comprises a label-domain of 30 bases including a 3' terminal CT wherein the C is also labeled, the mole percent is 5/30=16.7 mole percent label. In the overall probe, the mole percent is 8.3.

In some embodiments of the present invention, several target genes are simultaneously analyzed by exposing a cell or tissue sample to a plurality of nucleic acid probes that have been labeled with a plurality of different nucleic acid tags. For example, a plurality of nucleic acid probes can be labeled with a plurality of fluorescent compounds having different emission wavelengths, thereby permitting simultaneous multicolored analysis to be performed in a single step on a single target cell or tissue sample.

The oligonucleotide probes and oligonucleotide probe collections of the present invention may be used in ISH analysis to detect or localize nucleic acid target genes within a cell or tissue sample. ISH may be performed as described, for example, in *In Situ Hybridization Medical Applications* (G. R. Coulton and J. de Belleroche, eds., Kluwer Academic Publishers, 1992); *In Situ Hybridization: In Neurobiology; Advances in Methodology* (J. H. Eberwine, K. L. Valentino, and J. D. Barchas, eds., Oxford University Press, 1994); or *In Situ Hybridization: A Practical Approach* (D. G. Wilkinson, ed., Oxford University Press, 1992)).

The preferred embodiment of the probes and probe collections of the present invention are best understood by referring to FIGS. 1-21 and Examples 1-2. The Examples, which follow, are illustrative of specific embodiments of the invention, and various uses thereof. They are set forth for explanatory purposes only, and are not to be taken as limiting the invention.

EXAMPLE 1

Probe Collection Preparation

Probe collections consisting of a plurality of oligonucleotide probes of 55 to 60 bases in length were designed as follows. In this Example, each oligonucleotide probe possessed two distinct domains: a 5' (or labeling) domain and a 3' (or target gene-specific) domain (See FIG. 1).

In this embodiment, the labeling domain consists of the sequence $(CTATTTT)_nCT$, wherein the cytosine nucleotide represents a fluorescein-cytosine nucleotide conjugate and the fluorescein molecule is linked at the N4 position of cytosine through an OBEA linkage.

The target gene-specific domain consists of a 25-30 base sequence that is complementary to a specific nucleic acid target gene. Oligonucleotide probes were designed to possess target gene-specific domains corresponding to the human immunoglobulin kappa light chain variable region (See Table 1; oligonucleotide probes 401-416), the human immunoglobulin lambda light chain variable region (oligonucleotide probes 501-515), human cytomegalovirus (CMV) sequences (oligonucleotide probes 221-241), human Esptein-Barr virus (EBV) EBER (Epstein-Barr early RNA) sequences (oligonucleotide probes 100A2, 100C2, 100A1, and 100B1), human repetitive Alu sequences (oligonucleotide probes 301 and 302), and poly d(T) (oligonucleotide probe 320).

EXAMPLE 2

Label-Domain Design

Alu Repetitive Sequence Probe

Four probes all against the Alu human repetitive sequence were used to evaluate label-domain design. The probes numbered 301 (SEQ ID NO: 55), 301A (SEQ ID NO:116), 301A2/2 (SEQ ID NO: 121), and 301A3/2 (SEQ ID NO: 122) are shown in Table 1.

The four probes were evaluated at the concentrations of 100, 75, 50, and 25 ng/ml per mL of probe in the reaction, respectively. This hybridization analysis was done manually, using standard protocols. The target, paraffin-embedded cell line MBA MD 468 (Oncor INFORM™ Her-2/neu Control Slides, Cat. No. S8100, Level 1, available from Ventana Medical Systems, Inc., Tucson, Ariz.) was the target sample and was processed by removing paraffin by standard xylene methods. The tissue was subjected to Ventana's Protease 1 for 12 minutes at 50 degrees C. as a 1:2 dilution with Ventana's APK buffer. The hybridization reaction was accomplished with the addition of probe diluent as 100 μl probe (25% formamide, 5% dextran sulfate, 2×SSC, 1% Triton) to a residual 100 μl volume of 2×SSC/Triton X-100. The slide was heated to 85 degrees C. for 5 minutes and then incubated for 1 hr at 37 degrees C. Standard SSC washes followed for removing excess probe. The hybrids were detected with an antibody against FITC. The mouse antibody was detected colorimetrically using Ventana Enhanced Alkaline Phosphatase Blue Detection (cat#760-061). Unless otherwise indicated, all reagents were obtained from Ventana Medical Systems, Inc., Tucson, Ariz. The results were observed by colorimetric detection using brightfield microscopy.

The results of these experiments were that signal intensity was a function of the total number of fluorescein hapten conjugated to the probe and signal was of the specific label-domain design. The greater the number of fluoresceins per probe molecule, the greater the signal observed. Comparison of design and placement of haptens on the probe showed that this was not a factor in signal intensity. The two probes that contained five fluoresceins, (301A3/2 (SEQ ID NO: 122) and 301 (SEQ ID NO:55) both yielded equivalent signal. These two probes yielded greater signal that seen for 301A2/2, a probe with a split label-domain design with four fluoresceins. The probe 301A2/2 yielded a signal greater than probe 301A a probe with a single label-domain design at the 5' end and with three fluoresceins.

EXAMPLE 3

Label Domain Design

EBER Probes

This experiment compared two label-domain designs and sequences to determine whether greater spacing between the fluorescein haptens improves the production of signal during probe detection steps during in situ hybridization analysis.

The tissue used was an EBV-infected human spleen tissue fixed in neutral buffered formalin paraffin embedded section of 4-micron thickness placed on silane plus glass microscope slides. The tissue sections were deparaffinized on a Ventana DISCOVERY™ machine, followed by a 6-min digestion with Ventana's Protease 1, at a temperature of 37 C. The probe was dissolved in hybridization buffer diluent at a concentration of 50 ng/mL as a 100 μl applied to an equal volume of 2×SSC/Triton X-100 residual volume left on the slide after prepared by the Ventana Medical Systems, Inc. automated ISH staining system, Discovery. The probe diluent-mixed with the residual volume on slide for 6 min at 37 C, then the solution was heated to 85 C and held there for a total of 10 min. The slide was then taken to a 37 C temperature and held at that temperature for 1 hour. All of these aqueous reactions on the slide were all done under a film of LIQUID COVER-SLIP™, to prevent evaporative loss of water during processing. Each slide after hybridization was washed 3 times with 2×SSC/Triton solution, with a 6 min incubation between each wash, the slide volume being approximately 300 μl (+/−10% vol). The hybrids were detected with an antibody against FITC. The mouse antibody was detected colorimetrically using Ventana Enhanced Alkaline Phosphatase Blue Detection (cat#760-061).

The two oligonucleotide probes used for this study probe 100A1 (SEQ ID NO: 53) and 1002A32 (SEQ ID NO: 120). The two differences between these probes were the label-domain sequence and structure. The probe 100A1 label domain was 5' to gene target domain, contained 5 fluoresceins attached to cytosine residues via the OBEA linker, with the sequence formula of $(CTATTTT)_4CT$ (SEQ ID NO: 58). The label domain of the oligo probe 1002A32, was similar, (SEQ ID NO:125). Besides the different sequence the primary difference was that the fluorescein labeled cytosines were spaced 10 bases apart compared to the oligo 100A1 the cytosine spacing was closer at 7 bases apart. The result of this comparison as deduced by H score analysis were that these oligonucleotide were equivalent as to the amount of signal generated on the slide. The data was that for 100A2, for the 368 cells analyzed in a total of 3 fields the H score was 106, and for probe 1002A32 for the 345 cell analyzed in three field the H score was 109. The H score is a spectrographic analysis done with microscope that factors into the score background to signal ratio on the tissue section to yield a relative comparison of total target specific signal on the slide. (See reference Giroud, F. Perrin C, and Simony Lafontaine, J.; Quantitative Immunocytochemistry and Immunohistochemistry. Third Conference of the European Society for Analytical Cellular Pathology, 1994; and AutoCyte Quic Immuno User's Manual, 1998, document number PA-029, Co AutoCyte Inc. Burlington N.C. 2721). The histograms and the score sheet indicated that each oligo were equally efficient in yielding a colorimetric signal. This indicates that the position of the label domain can be either 3 prime or 5 prime to the gene target sequence or the gene target sequence can be positioned between two label domains.

EXAMPLE 4

In Situ Hybridization

The probe collections prepared in Example 1 were first diluted in a solution consisting of 20% dextran sulfate (wt/vol), 50% formamide (vol/vol), 2×SSC, 10 mM Tris-HCl, 5 mM EDTA, and 0.05% Brij-35, at a final pH of 7.3. Probe collections were then mixed with an equal volume of a solution consisting of 2×SSC and 0.05% Triton X-100.

Samples for ISH analysis were prepared by cutting formalin-fixed and paraffin-embedded cells or tissue samples into 4 μm sections and placing the sections onto a glass slide. Subsequent processing and ISH of samples was carried out in an automated device, such as the DISCOVERY™ Automated ISH/IHC Stainer (Ventana Medical Systems, Inc., Tucson, Ariz.) described in co-owned and co-pending U.S. Patent App. Ser. Nos. 60/076,198 and 09/259,240, both incorporated herein by reference. To remove paraffin from the samples, the slides were immersed in an aqueous solution, heated for approximately 20 minutes, and then rinsed. The automated deparaffinization procedure is more fully described in U.S. Ser. Nos. 60/099,018, and 09/259,240 both incorporated herein by reference. The samples were then treated with protease and the slides were heated to 85° C. (for hybridization to RNA target genes) or 90-95° C. (for hybridization to DNA target genes) for 4 to 10 minutes.

Hybridization reactions were typically performed in a hybridization buffer consisting of 10% dextran sulfate (wt/vol), 25% formamide (vol/vol), 2×SSC, 5 mM Tris, 2.5 mM EDTA, 0.025% Brij-35, 0.25% Triton X-100, and between 25 to 125 ng/mL of each individual probe molecule. ISH reactions were performed at between 37° C. to 54° C. For ISH using the probe collections described in Example 1, hybridization reactions were optimally carried out for 1 hr at 47° C. (except for the poly d(T) probe, wherein the hybridization reaction was optimally carried out at 37° C. for 1 hr).

The hybridization of fluorescein-labeled probe molecules to a particular target gene in the sample was detected by using a sequential series of binding proteins, i.e., secondary antibody detection. However, it is equally possible to use detect detection when visualizing the bound probes. In secondary detection, first, an anti-fluorescein mouse monoclonal antibody directed against the fluorescein-labeled probe molecule was added to the sample. Next, a biotin-labeled polyclonal goat antibody directed against the mouse antibody was added to the sample. Finally, hybridization reactions were colorimetrically detected using a 5-bromo-4-chloro-3-indolyl phosphate/nitroblue tetrazolium (BCIP/NBT) substrate. This technique, termed "secondary antibody detection," is routine for one of skill in the art. Primary and secondary antibodies are available from numerous suppliers, including Ventana Medical Systems, Tucson, Ariz., which are optimized for use on the Ventana autostaining systems (ES®, NexES®, DISCOVERY™, and BENCHMARK™).

FIGS. 2-21 illustrate the results obtained for in situ hybridization analysis of various cell lines or tissue samples using the probes disclosed and claimed herein having the structural motif illustrated in FIG. 1 or probe collections consisting of such probes.

FIG. 1 illustrates a generic probe structure of the two-domain probe design. This is the oligonucleotide design used for the probes in the gene specific cocktails described in the following examples. Each probe is composed of two domains: a 5' labeling domain and a 3' target gene target gene-specific domain. The labeling domain consists of this specific sequence $(CTATTTT)_n CT$, wherein the cytosine nucleotide is a cytosine-hapten conjugate, the hapten being fluorescein in this embodiment. This illustration specifically shows nucleic acid sequences for the 301 (SEQ ID NO: 55) and 302 (SEQ ID NO: 56) probes, each of which possesses target gene gene-specific domains corresponding to human repetitive Alu sequences and labeling domains having a fluorescein hapten.

Figure 2:
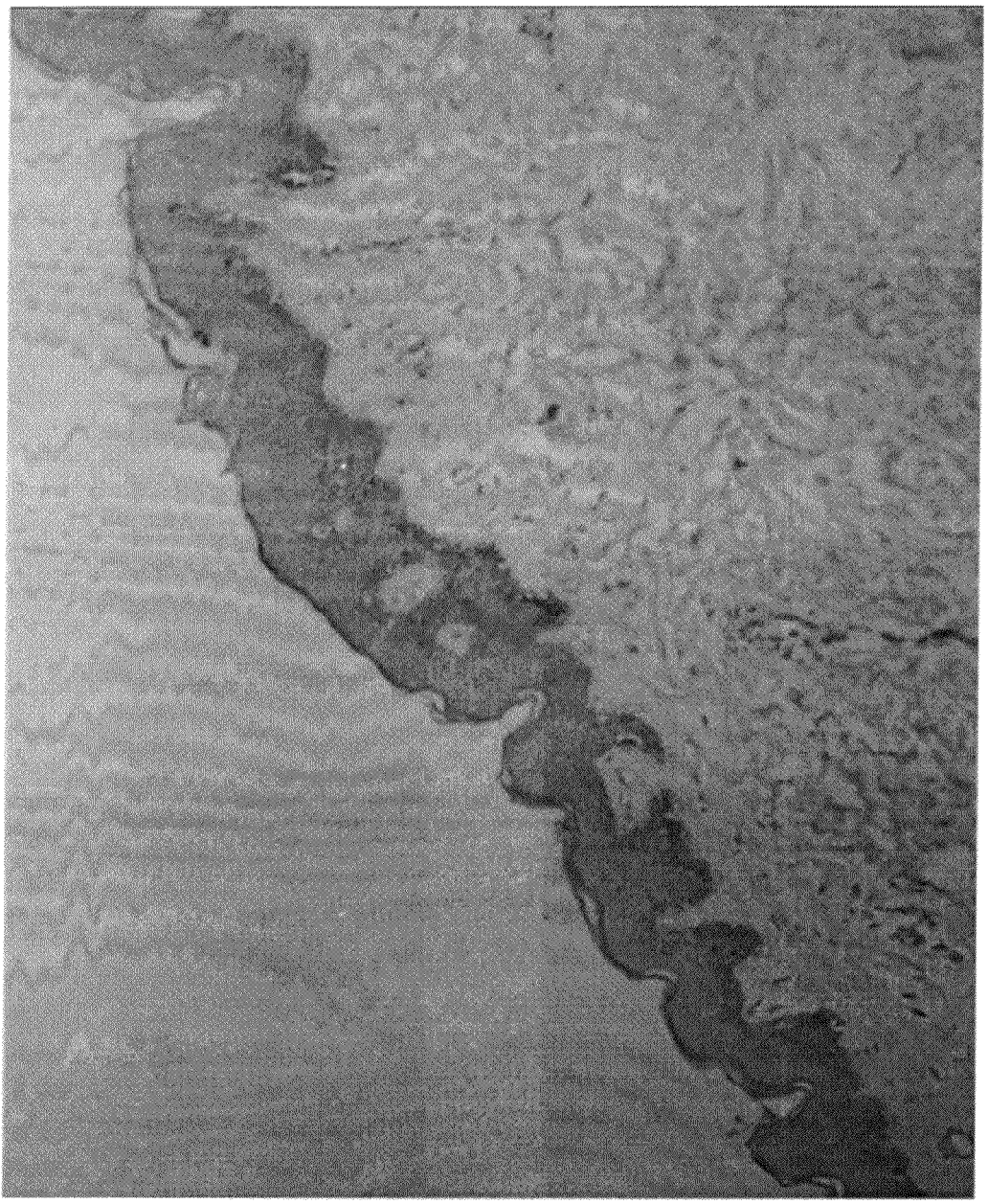
FIG. 2 illustrates the results obtained for in situ hybridization (ISH) analysis of human skin tissue using a probe comprising the labeling domain (330 probe; SEQ ID NO: 58). The absence of a detectable signal indicates that the sequence formula, $(CTATTTT)_n CT$, of the labeling domain common to the oligonucleotides used in these ISH examples is non-specific, and non-reactive in its ability to form Watson-Crick base pairing with human nucleic acid sequences because it does not hybridize.

FIG. 2 illustrates the results obtained for in situ hybridization (ISH) analysis of human skin tissue using a probe comprising the labeling domain (330 probe; SEQ ID NO: 58). The absence of a detectable signal indicates that the sequence formula, $(CTATTTT)_n CT$, of the labeling domain common to the oligonucleotides used in these ISH examples is non-specific, and non-reactive in its ability to form Watson-Crick base pairing with human nucleic acid sequences because it does not hybridize.

Figure 3:
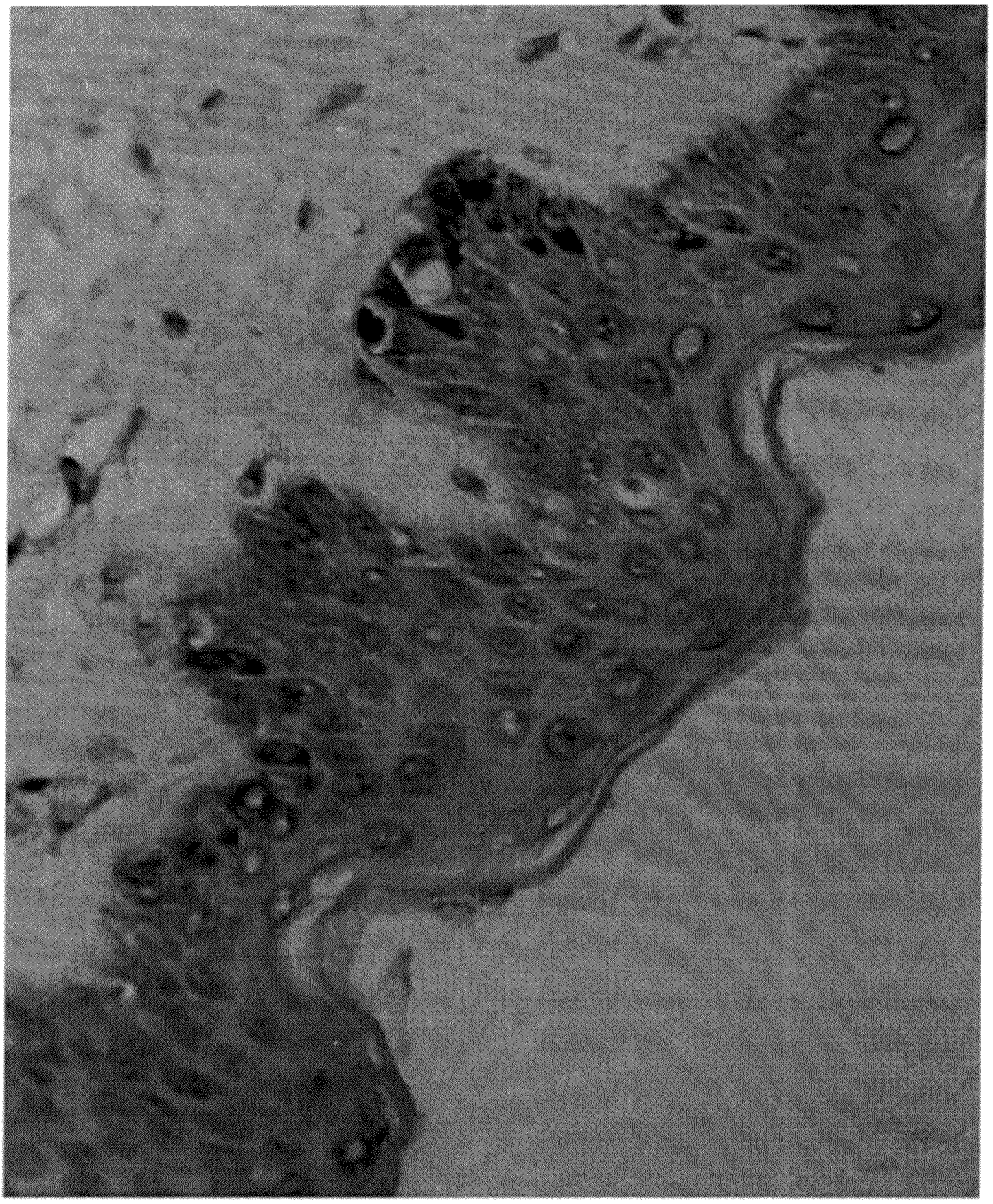
FIG. 3 illustrates the results obtained for ISH analysis of human skin tissue using a probe comprising the labeling domain and a poly d(T) target gene-specific domain (320 probe; SEQ ID NO: 57). The presence of a detectable signal localized to the cytoplasm indicates that this probe is capable of specifically hybridizing to polyadenylated region of messenger RNA.

FIG. 3 illustrates the results obtained for ISH analysis of human skin tissue using a probe comprising the labeling domain and a poly d(T) target gene-specific domain (320 probe; SEQ ID NO: 57). The presence of a detectable signal localized to the cytoplasm indicates that this probe is capable of specifically hybridizing to polyadenylated region of messenger RNA.

Figure 4B:
FIGS. 4A-4B illustrate the results obtained for ISH analysis of human skin tissue using the 320 probe, wherein the tissue sample was not treated with ribonuclease A prior to in situ hybridization (A), or was treated with ribonuclease A prior to in situ hybridization (B). The decrease in detectable signal in (B) indicates that this probe specifically hybridizes to polyadenylated region common to messenger RNA.
Figure 4A:
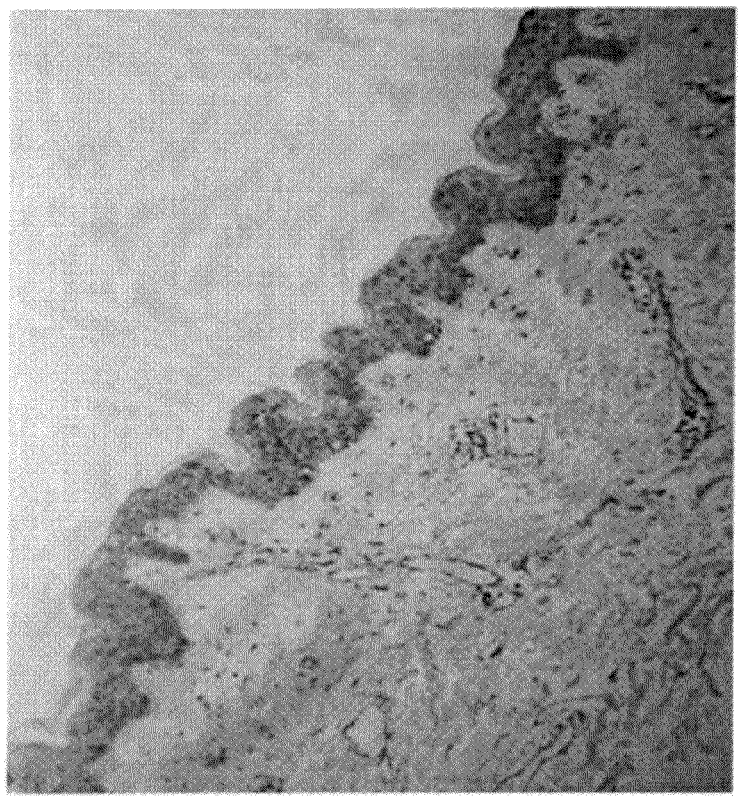

FIGS. 4A-4B illustrate the results obtained for ISH analysis of human skin tissue using the 320 probe, wherein the tissue sample was not treated with ribonuclease A prior to in situ hybridization (A), or was treated with ribonuclease A prior to in situ hybridization (B). The decrease in detectable signal in (B) indicates that this probe specifically hybridizes to polyadenylated region common to messenger RNA.

Figure 5B:
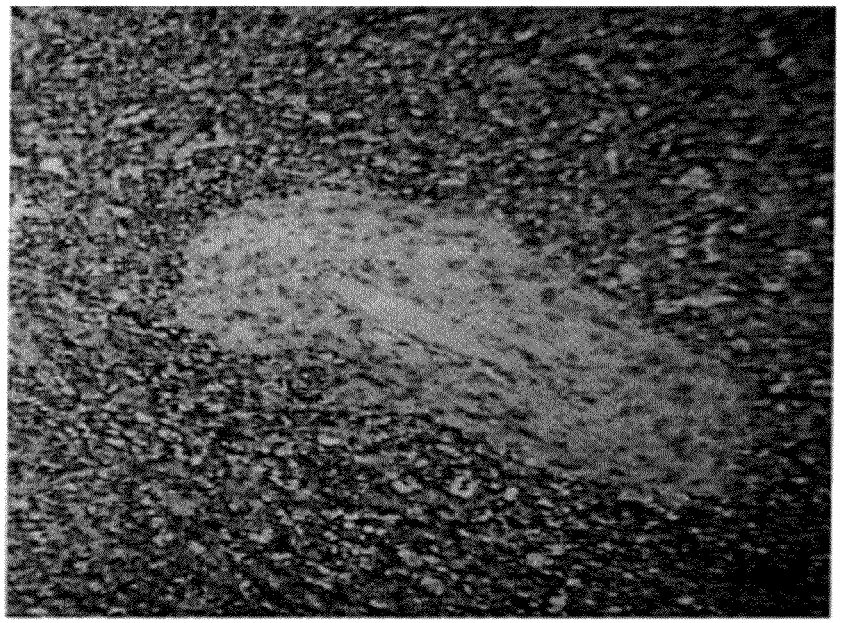
FIGS. 5A-5B illustrate the results obtained for ISH analysis of human spleen tissue using the 320 probe, wherein the hybridization and stringency wash were performed at room temperature (A), or at 37° C. (B). This result illustrates that the intensity of color is related to the stringency of hybridization conditions, with the more intense color indicating less stringent conditions.
Figure 5A:
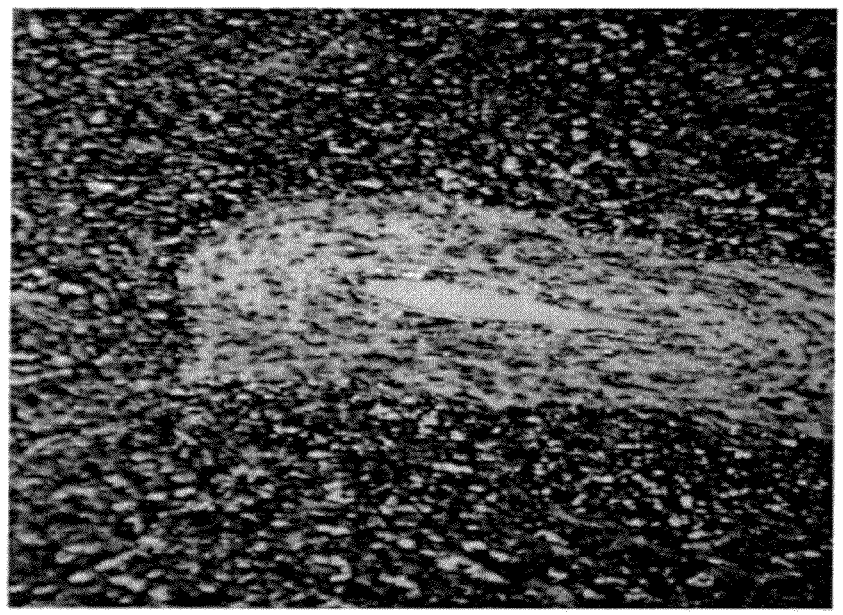

FIGS. 5A-5B illustrate the results obtained for ISH analysis of human spleen tissue using the 320 probe, wherein the hybridization and stringency wash were performed at room temperature (A), or at 37° C. (B). This result illustrates that the intensity of color is related to the stringency of hybridization conditions, with the more intense color indicating less stringent conditions.

Figure 6:
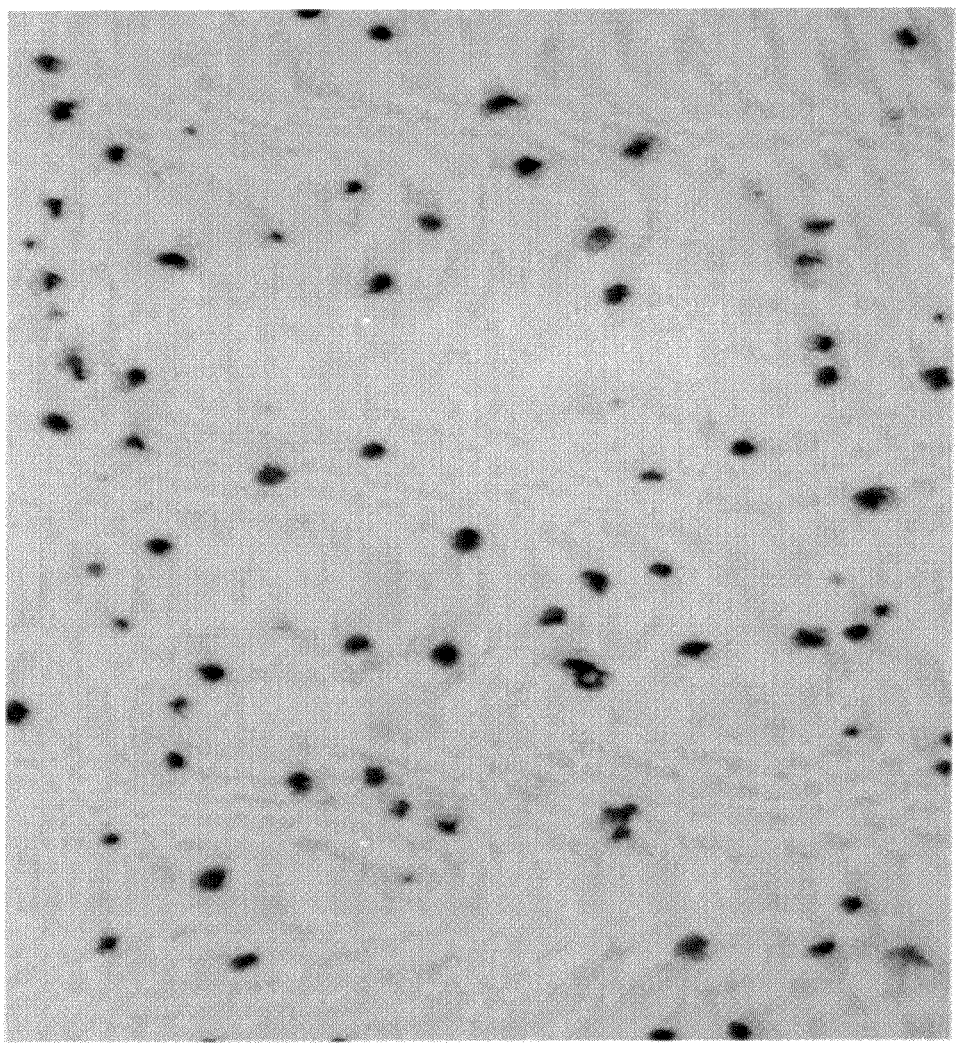
FIG. 6 illustrates the results obtained for ISH analysis of the human Raji cell line using the 320 probe. This shows that this probe design also is functional with embedded cell lines as well as embedded tissue.

FIG. 6 illustrates the results obtained for ISH analysis of the human Raji cell line using the 320 probe. This shows that this probe design also is functional with embedded cell lines as well as embedded tissue.

Figure 7:
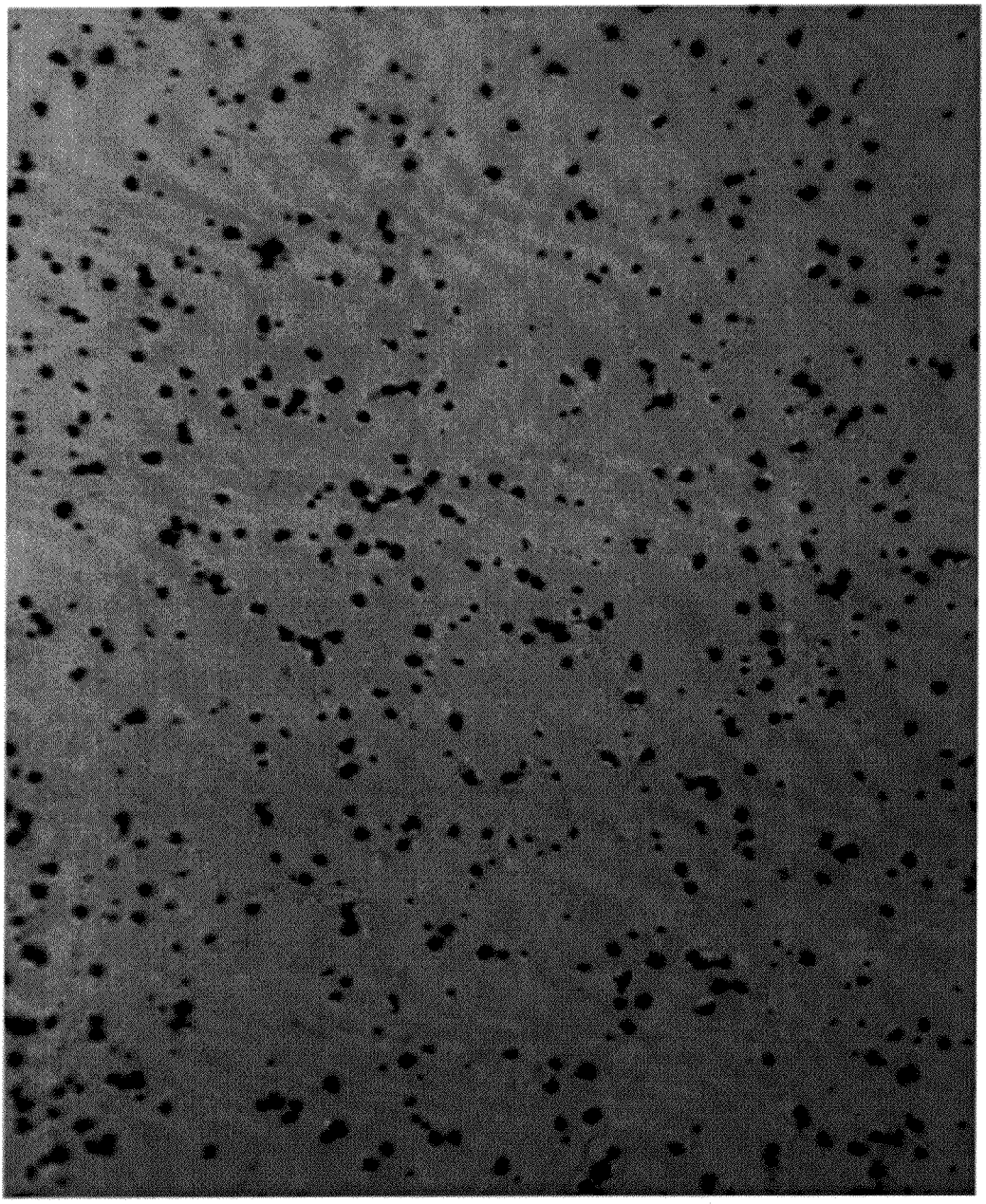
FIG. 7 illustrates the results obtained for ISH analysis of the human Raji cell line using a probe collection consisting of the 301 and 302 probes.

FIG. 7 illustrates the results obtained for ISH analysis of the human Raji cell line using a probe collection consisting of the 301 and 302 probes.

Figure 8:
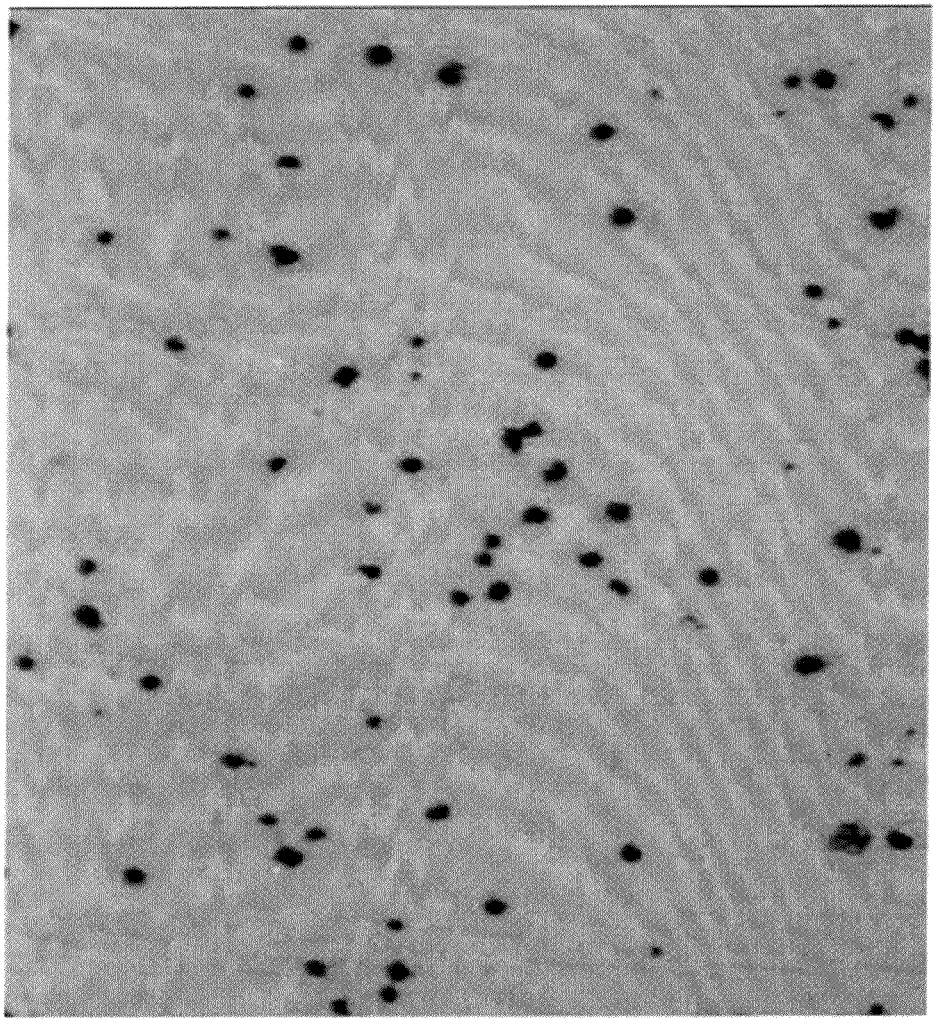
FIG. 8 illustrates the results obtained for ISH analysis of the human HT cell line using a probe collection consisting of the 301 and 302 probes.

FIG. 8 illustrates the results obtained for ISH analysis of the human HT cell line using a probe collection consisting of the 301 and 302 probes.

Figure 9:
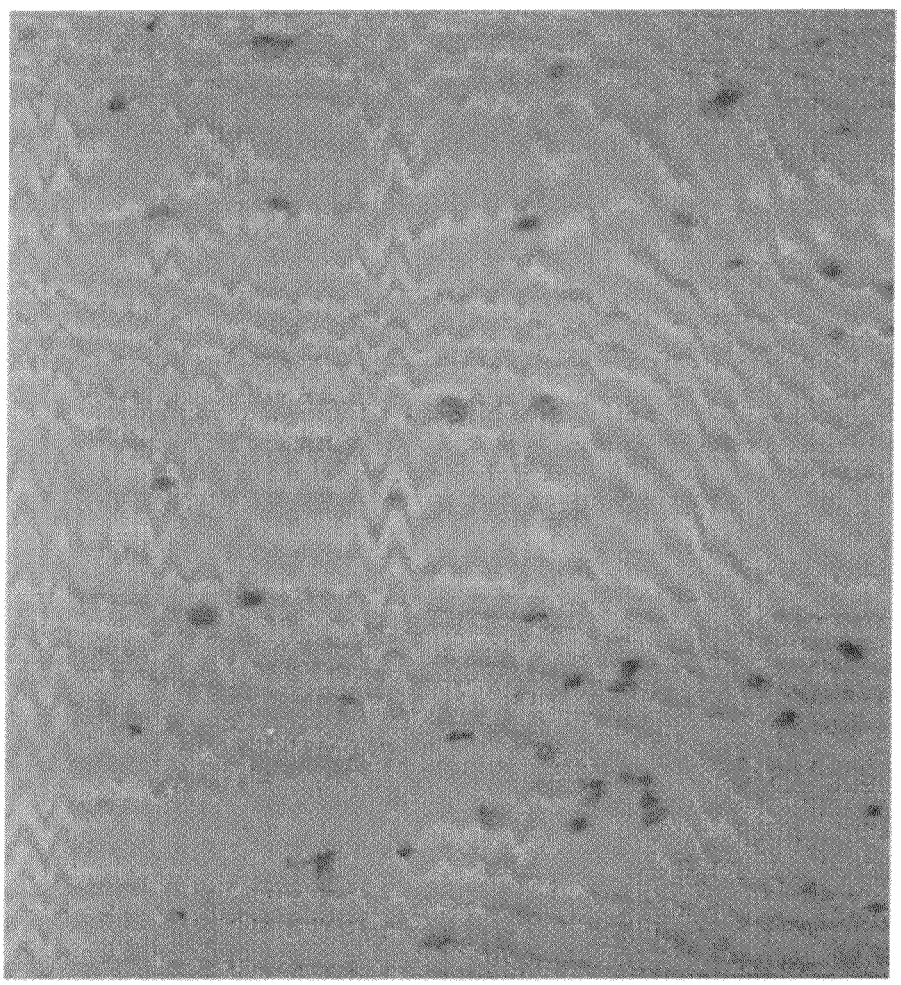
FIG. 9 illustrates the results obtained for ISH analysis of a rat cell line using a probe collection consisting of the 301 and 302 probes. The absence of a detectable signal indicates that this probe collection is specific for human nucleic acid sequences.

FIG. 9 illustrates the results obtained for ISH analysis of a rat cell line using a probe collection consisting of the 301 and 302 probes. The absence of a detectable signal indicates that this probe collection is specific for human nucleic acid sequences.

Figure 10:
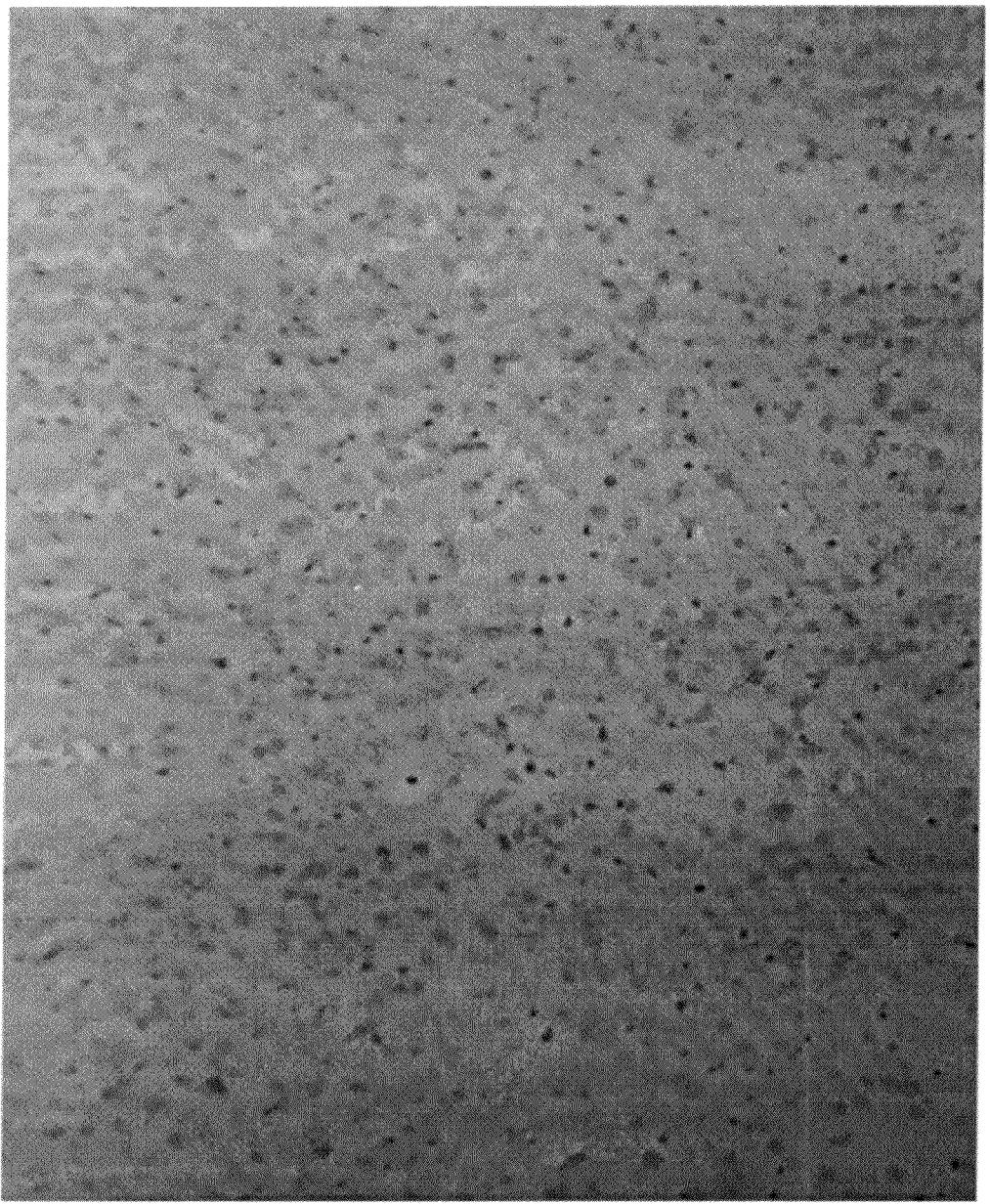
FIG. 10 illustrates the results obtained for ISH analysis of an Epstein-Barr virus (EBV)-negative human HT cell line using a probe possessing a target gene-specific domain corresponding to EBV EBER nuclear RNA (SEQ ID NOS: 51 through 54 inclusive).

FIG. 10 illustrates the results obtained for ISH analysis of an Epstein-Barr virus (EBV)-negative human HT cell line using a probe possessing a target gene-specific domain corresponding to EBV EBER nuclear RNA (SEQ ID NO: 51 through SEQ ID NO: 54).

Figure 11:
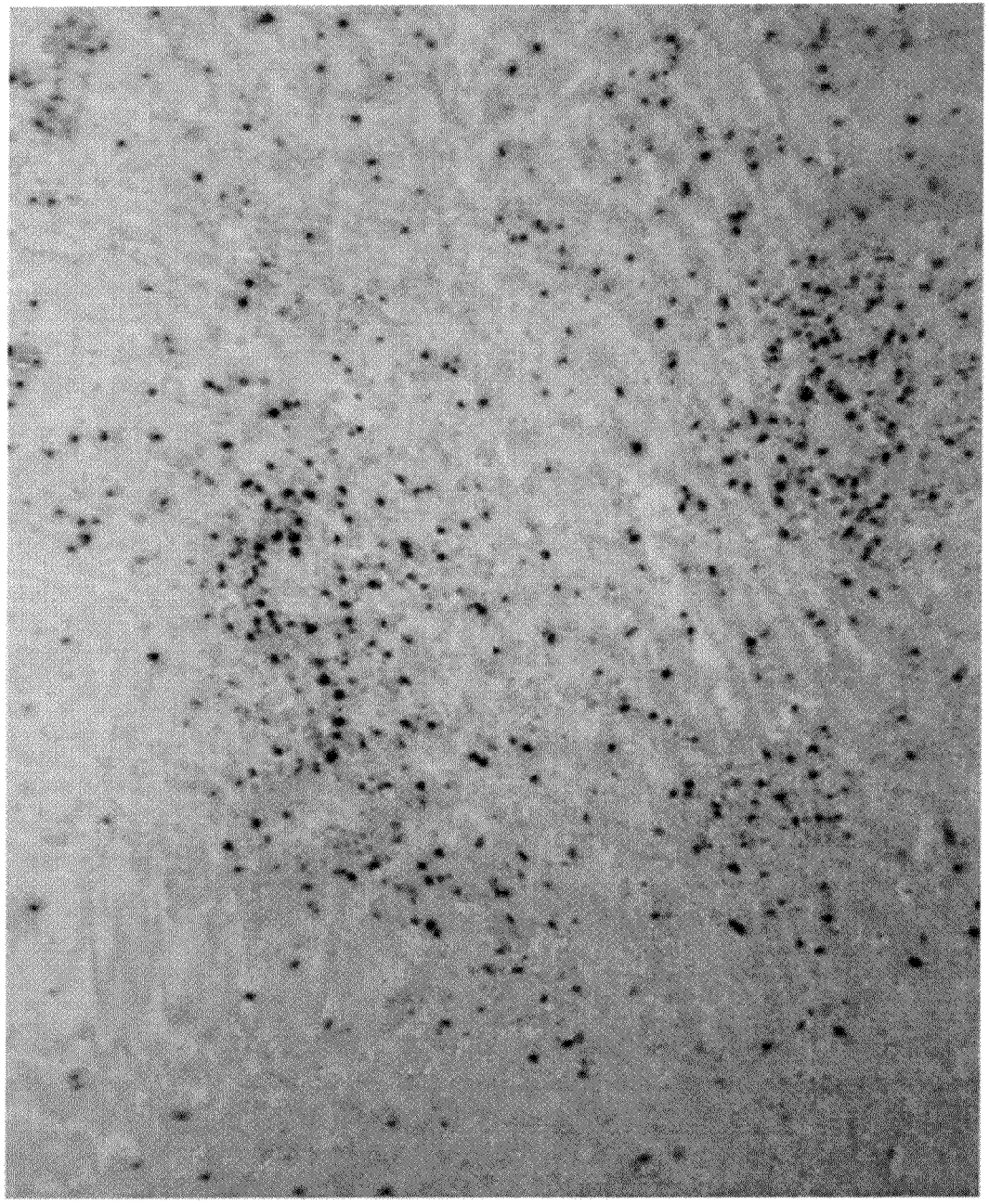
FIG. 11 illustrates the results obtained for ISH analysis of human spleen tissue using a probe collection consisting of probes possessing target gene-specific domains corresponding to EBV EBER 1 and 2 nuclear RNA (SEQ ID NOS: 51 through 54 inclusive).

FIG. 11 illustrates the results obtained for ISH analysis of human spleen tissue using a probe collection consisting of probes possessing target gene-specific domains corresponding to EBV EBER 1 and 2 nuclear RNA (SEQ ID NO:51 through SEQ ID NO:54).

Figure 12:
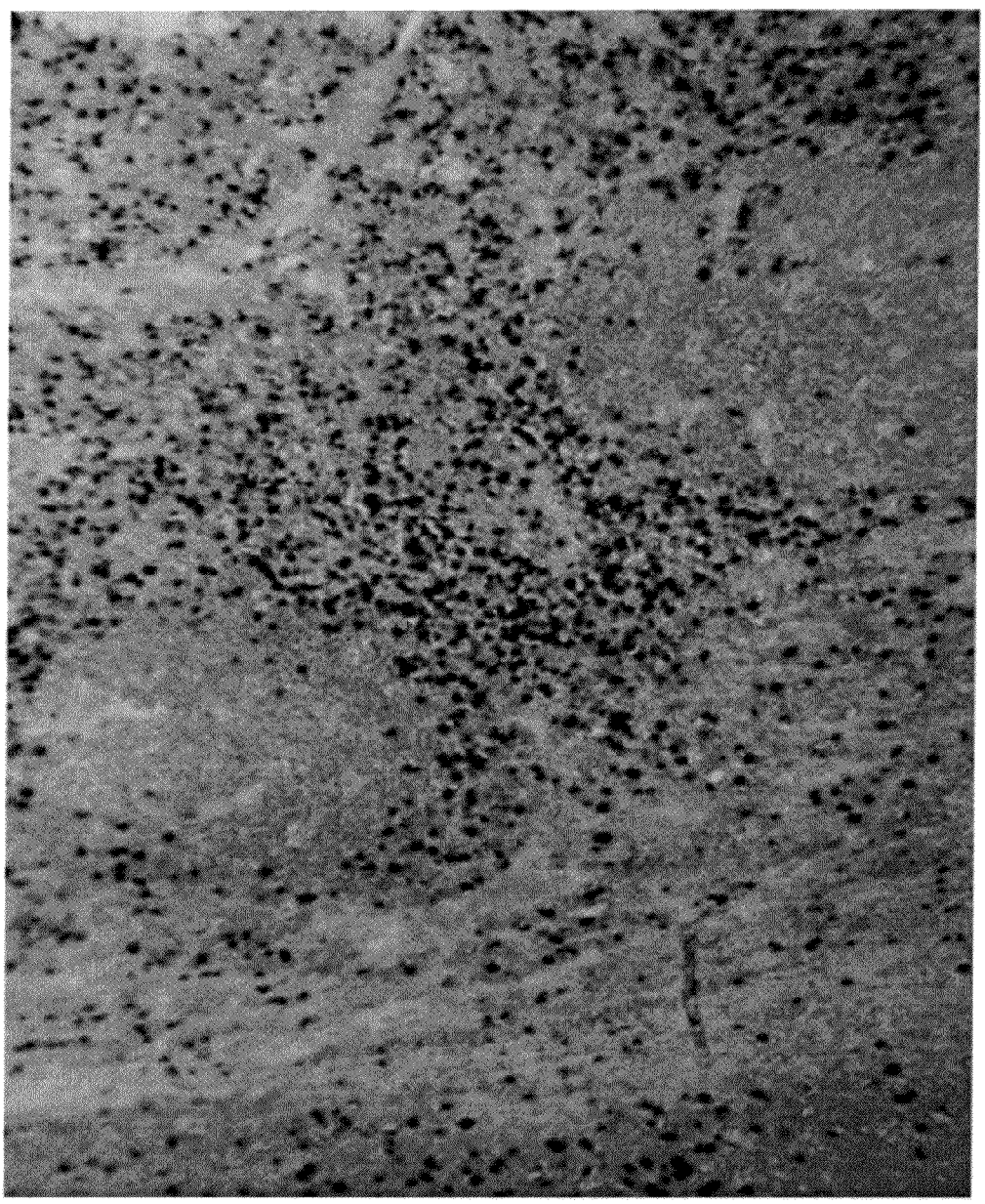
FIG. 12 illustrates the results obtained for ISH analysis of human tonsil tissue using a probe collection consisting of probes possessing target gene-specific domains corresponding to EBV EBER 1 and 2 nuclear RNA (SEQ ID NO:51 through SEQ ID NO:54).

FIG. 12 illustrates the results obtained for ISH analysis of human tonsil tissue using a probe collection consisting of probes possessing target gene-specific domains corresponding to EBV EBER 1 and 2 nuclear RNA (SEQ ID NO:51 through SEQ ID NO:54).

FIGS. 13A-13B illustrate the results obtained for ISH analysis of human spleen tissue using a probe collection consisting of probes possessing target gene-specific domains corresponding to EBV EBER 1 and 2 nuclear RNA (SEQ ID NO:51 through SEQ ID NO:54), wherein the tissue sample was not treated with ribonuclease A prior to in situ hybridization (A), or was treated with ribonuclease A prior to in situ hybridization (B). The decrease in detectable signal in (B) indicates that this probe specifically hybridizes to human EBER 1 and EBER 2 nuclear RNA.

Figure 14:
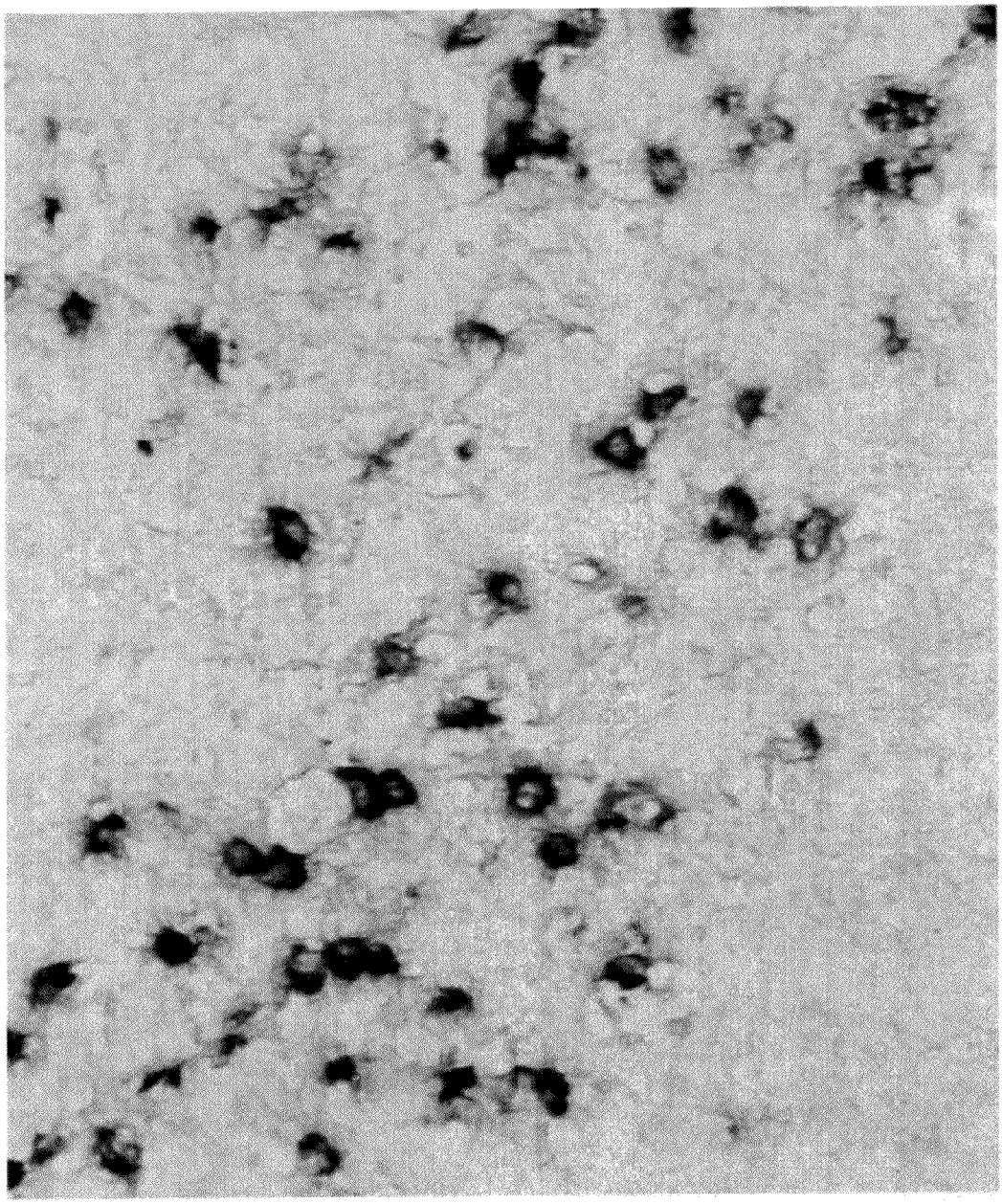
FIG. 14 illustrates the results obtained for ISH analysis of kappa light chain-positive human tonsil tissue using a probe possessing a target gene-specific domain corresponding to human immunoglobulin lambda light chain mRNA (SEQ ID NO: 15).

FIG. 14 illustrates the results obtained for ISH analysis of kappa light chain-positive human tonsil tissue using a probe possessing a target gene-specific domain corresponding to human immunoglobulin lambda light chain mRNA (SEQ ID NO:15).

Figure 15B:
FIG. 15 illustrates the results obtained for ISH analysis of lymphoma tissues using a probe collection consisting of probes possessing target gene-specific domains corresponding to human immunoglobulin kappa light chain mRNA (SEQ ID NOS: 2-4, SEQ ID NOS:7-12, SEQ ID NOS: 14, 15). The lymphoma tissue in (A) over expresses the kappa light chain and the tissue in (B) over expresses the lambda light chain. The absence of a detectable signal in (B) indicates that the kappa light chain probe collection is specific to kappa light chain mRNA.
Figure 15A:
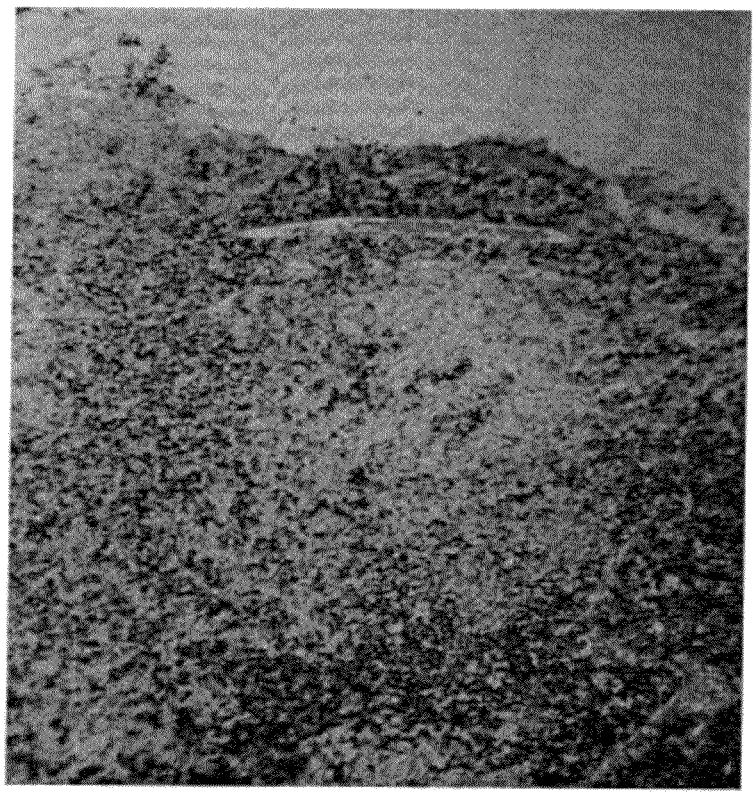

FIG. 15 illustrates the results obtained for ISH analysis of lymphoma tissues using a probe collection consisting of probes possessing target gene-specific domains corresponding to human immunoglobulin kappa light chain mRNA (SEQ ID NOS: 2-4, SEQ ID NOS:7-12, SEQ ID NOS: 14, 15). The lymphoma tissue in (A) over expresses the kappa light chain and the tissue in (B) over expresses the lambda light chain. The absence of a detectable signal in (B) indicates that the kappa light chain probe collection is specific to kappa light chain mRNA.

Figure 16:
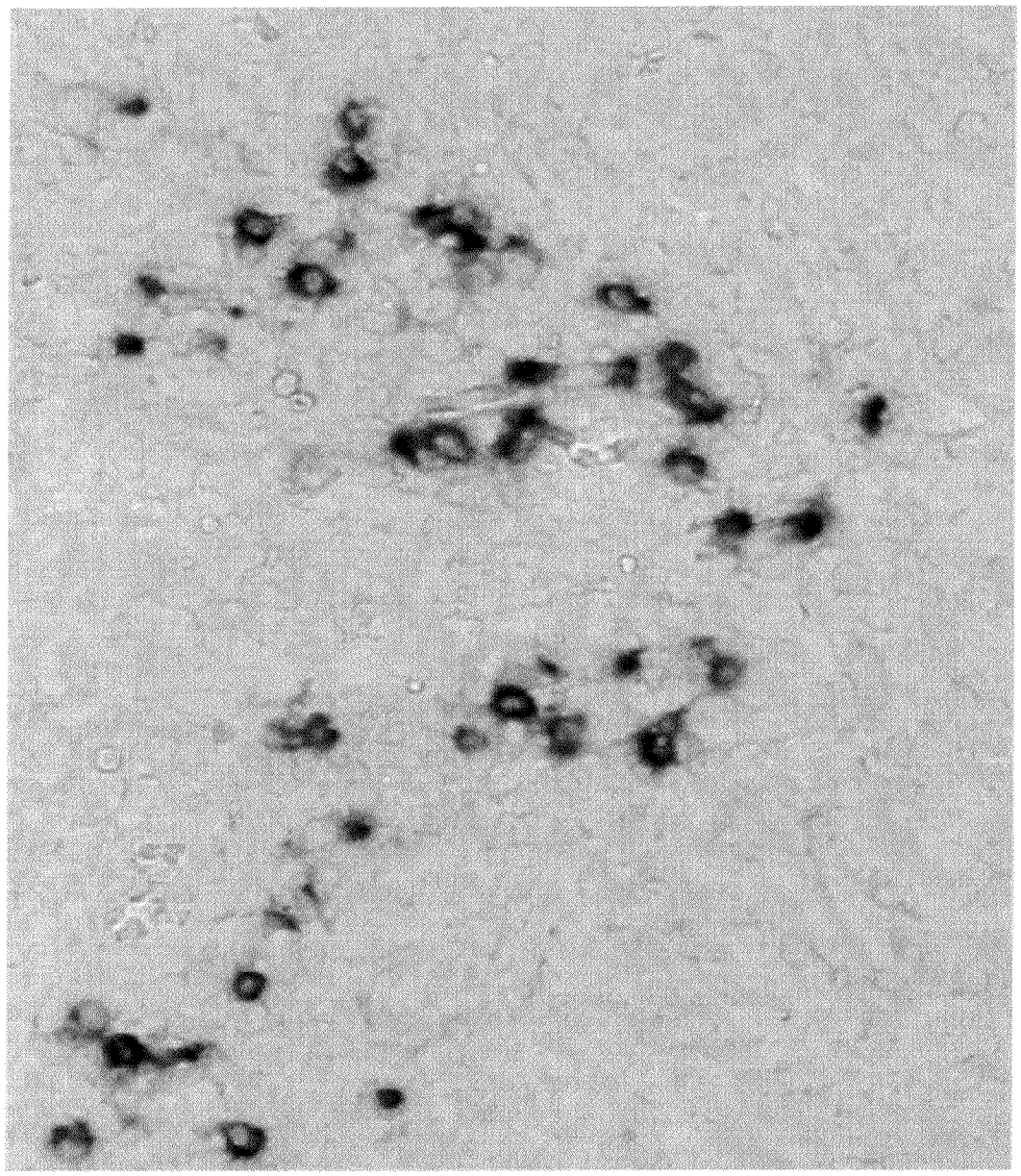
FIG. 16 illustrates the results obtained for ISH analysis of lambda light chain-positive human tonsil tissue using a probe possessing a target gene-specific domain corresponding to human immunoglobulin lambda light chain variable region mRNA (SEQ ID NOS:19 through 29).

FIG. 16 illustrates the results obtained for ISH analysis of lambda light chain-positive human tonsil tissue using a probe possessing a target gene-specific domain corresponding to human immunoglobulin lambda light chain variable region mRNA (SEQ ID NOS:19 through 29).

Figure 17:
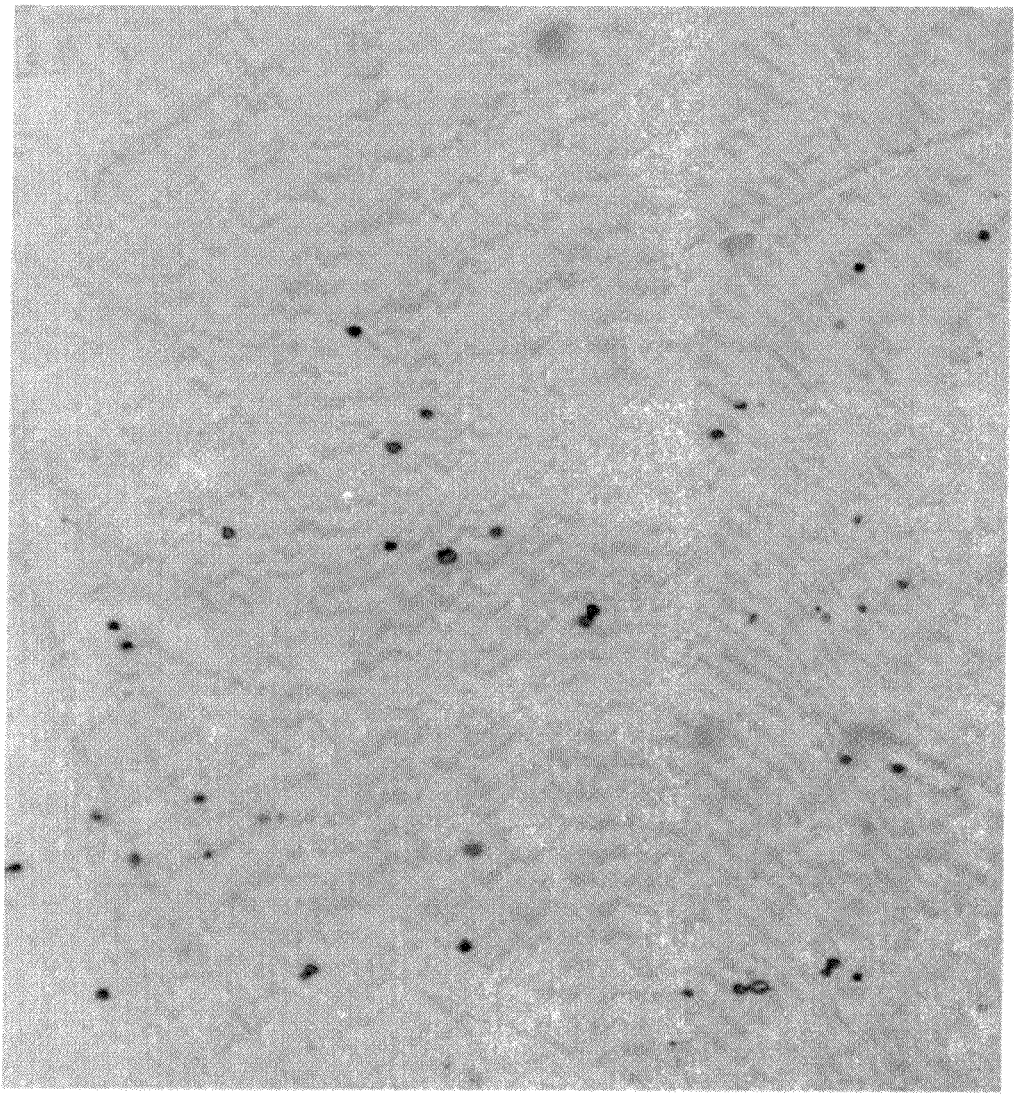
FIG. 17 illustrates the results obtained for ISH analysis of a lambda light chain-positive human RPMI 8226 cell line using a probe collection consisting of probes possessing target gene-specific domains corresponding to human immunoglobulin lambda light chain mRNA (SEQ ID NOS:19 through 29).

FIG. 17 illustrates the results obtained for ISH analysis of a lambda light chain-positive human RPMI 8226 cell line using a probe collection consisting of probes possessing target gene-specific domains corresponding to human immunoglobulin lambda light chain mRNA (SEQ ID NOS:19 through 29).

Figure 18B:
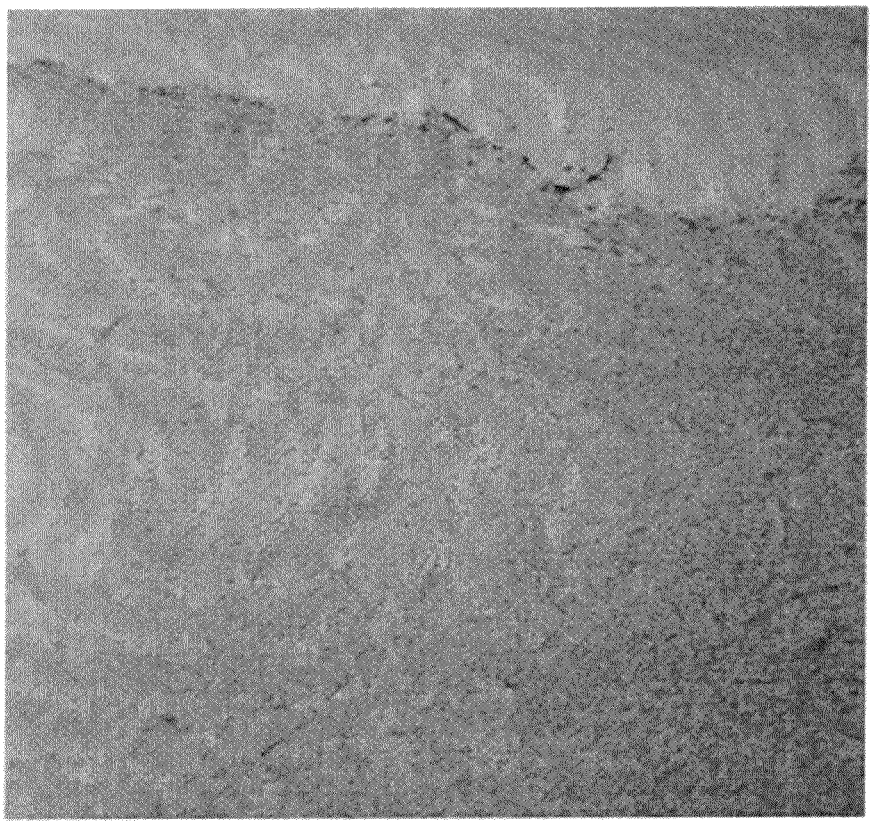
FIGS. 18A-18B illustrate the results obtained for ISH analysis of human spleen tissue using a probe collection consisting of probes possessing target gene-specific domains corresponding to human immunoglobulin lambda light chain mRNA (SEQ ID NOS:19 through 29). The tissue in (A) over expresses the lambda light chain and the tissue in (B) over expresses the kappa light chain. The absence of a detectable signal in (B) indicates that the lambda light chain probe collection is specific to human lambda light chain mRNA.
Figure 18A:
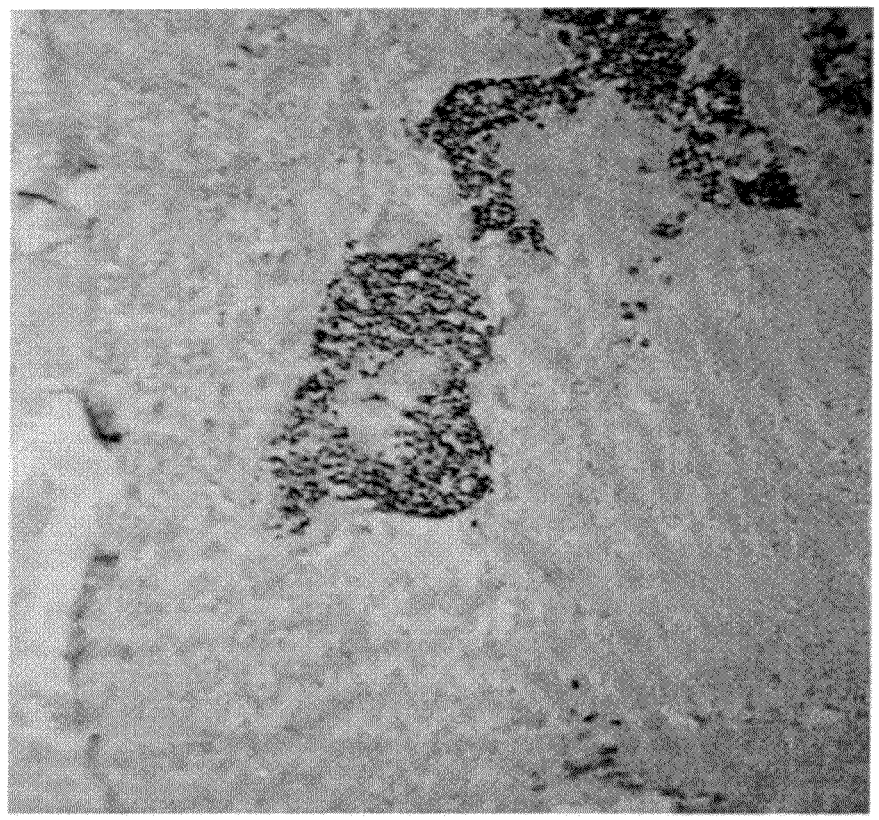

FIGS. 18A-18B illustrate the results obtained for ISH analysis of human spleen tissue using a probe collection consisting of probes possessing target gene-specific domains corresponding to human immunoglobulin lambda light chain mRNA (SEQ ID NOS:19 through 29). The tissue in (A) over expresses the lambda light chain and the tissue in (B) over expresses the kappa light chain. The absence of a detectable signal in (B) indicates that the lambda light chain probe collection is specific to human lambda light chain mRNA.

Figure 19:
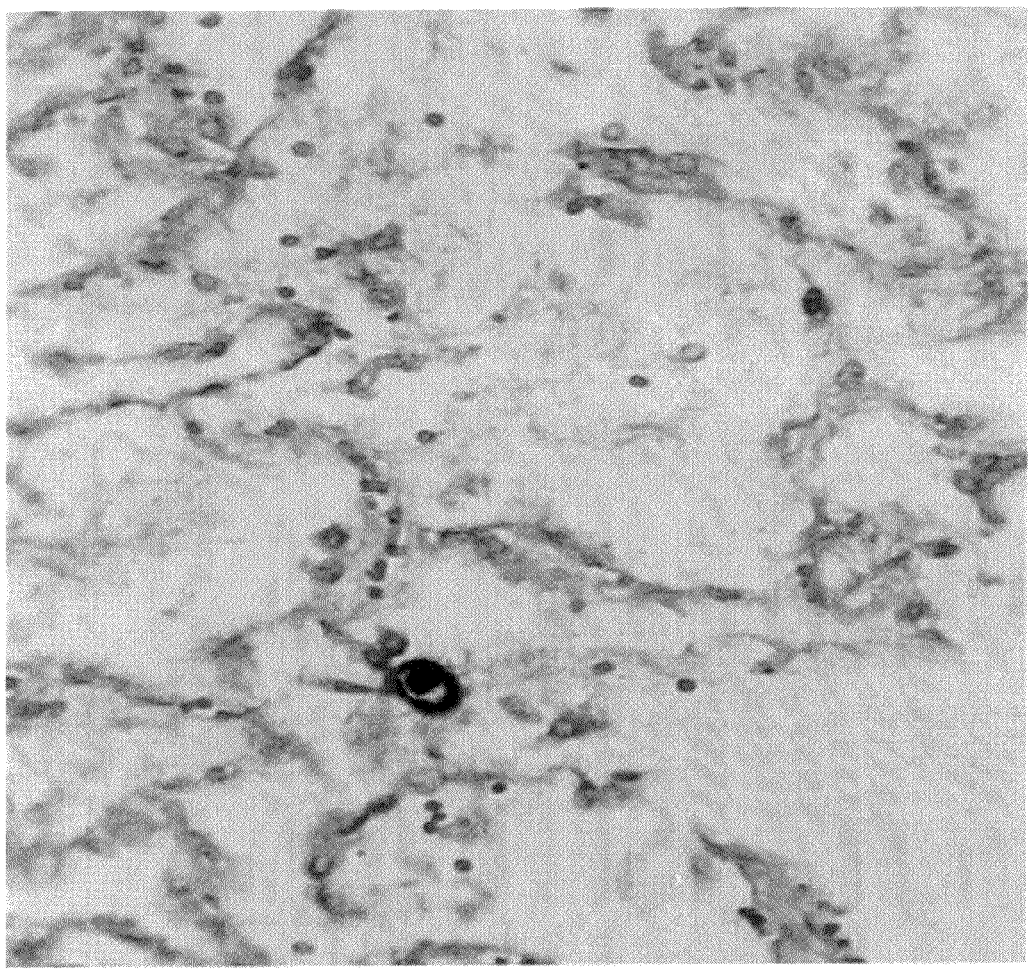
FIG. 19 illustrates the results obtained for ISH analysis of cytomegalovirus (CMV)-positive human lung tissue using a probe collection consisting of probes possessing target gene-specific domains corresponding to CMV immediate early RNA (SEQ ID NOS:30-32, SEQ ID NOS: 34-35, SEQ ID NO: 38, SEQ ID NO: 50). (CMV infected cell).

FIG. 19 illustrates the results obtained for ISH analysis of cytomegalovirus (CMV)-positive human lung tissue using a probe collection consisting of probes possessing target gene-specific domains corresponding to CMV immediate early RNA (SEQ ID NOS:30-32, SEQ ID NOS: 34-35, SEQ ID NO: 38, SEQ ID NO: 50). Arrow indicates CMV infected cell.

Figure 20:
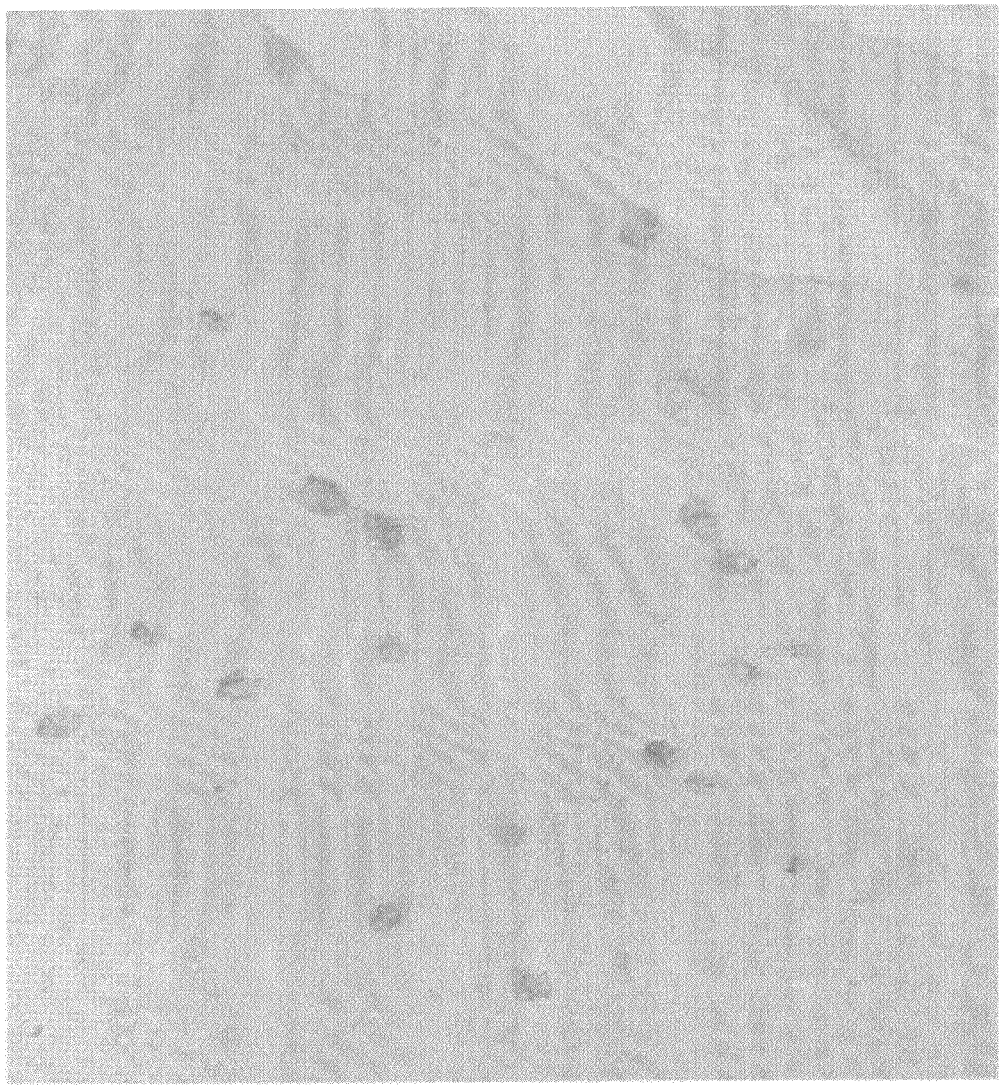
FIG. 20 illustrates the results obtained for ISH analysis of a rat 9G cell line in which the expression of CMV immediate early RNA has not been induced by cyclohexamide using a probe collection consisting of probes possessing target gene-specific domains corresponding to CMV immediate early mRNA (SEQ ID NOS:30-32, SEQ ID NOS: 34-35, SEQ ID NO: 38, SEQ ID NO: 50).

FIG. 20 illustrates the results obtained for ISH analysis of a rat 9G cell line in which the expression of CMV immediate early RNA has not been induced by cyclohexamide using a probe collection consisting of probes possessing target gene-specific domains corresponding to CMV immediate early RNA (SEQ ID NOS:30-32, SEQ ID NOS: 34-35, SEQ ID NO: 38, SEQ ID NO: 50).

Figure 21B:
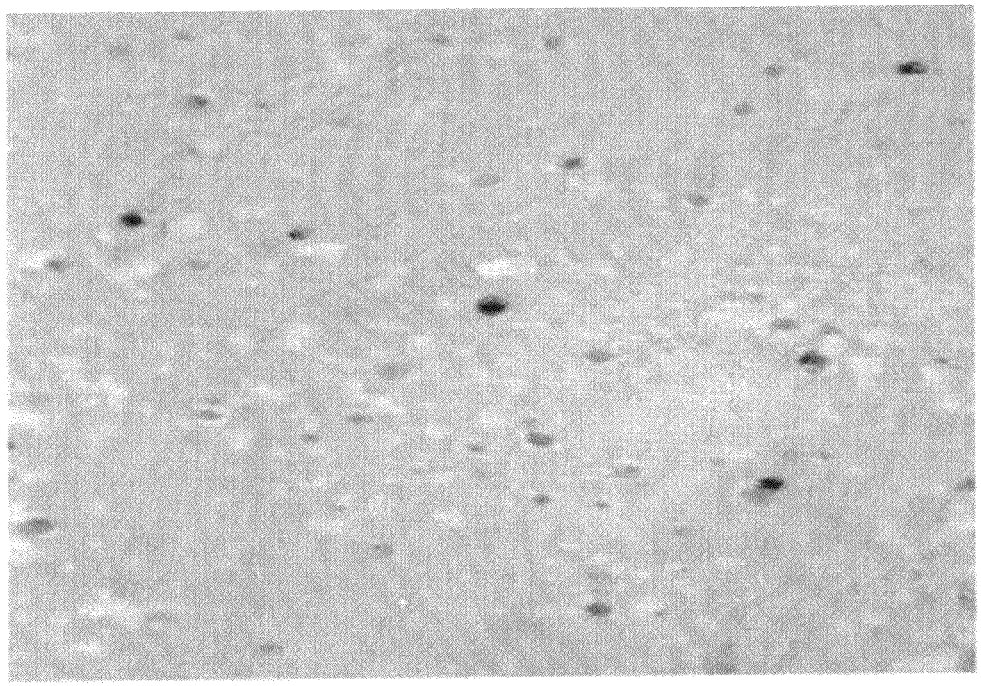
FIGS. 21A-21B illustrate the results obtained for ISH analysis of a rat 9G cell line in which the expression of CMV immediate early RNA has been induced by cyclohexamide using a probe collection consisting of probes possessing target gene-specific domains corresponding to CMV immediate early RNA (SEQ ID NOS:30-32, SEQ ID NOS: 34-35, SEQ ID NO: 38, SEQ ID NO: 50). The tissue in (A) is shown at a magnification of 40× and the tissue in (B) is shown at a magnification of 20×.
Figure 21A:
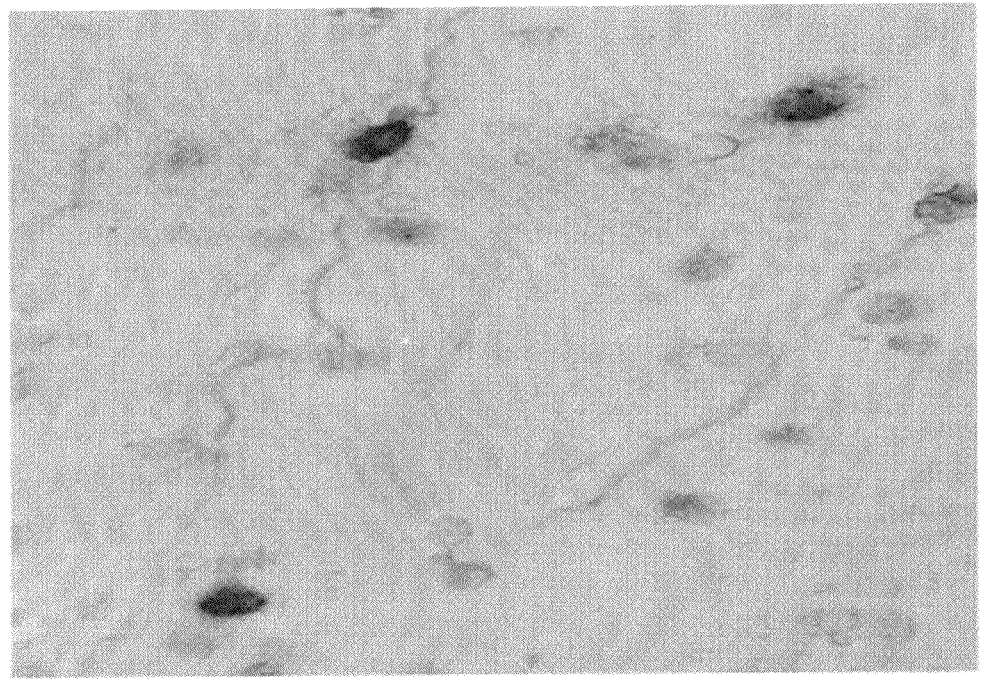

FIGS. 21A-21B illustrate the results obtained for ISH analysis of a rat 9G cell line in which the expression of CMV immediate early RNA has been induced by cyclohexamide using a probe collection consisting of probes possessing target gene-specific domains corresponding to CMV immediate early RNA (SEQ ID NOS:30-32, SEQ ID NOS: 34-35, SEQ ID NOS: 38 through 50) expression of the CMV immediate early RNA with cyclohexamide. The tissue in (A) is shown at a magnification of 40× and the tissue in (B) is shown at a magnification of 20×.

TABLE 1

| Probe ID | Sequence | SEQ ID |
|---|---|---|
| 401 | 5'-CTATTTTCTATTTTCTATTTTCTATTTTCT CCAGAGTAGCAGGAGCCCCAGGAGCTGAGC-3' | 1 |
| 402 | 5'-CTATTTTCTATTTTCTATTTTCTATTTTCT GGATGGAGACTGGGTCAACTGGATGTCACA-3' | 2 |
| 403 | 5'-CTATTTTCTATTTTCTATTTTCTATTTTCT GCAAGCGATGGTGACTCTGTCTCCTACAGC-3' | 3 |
| 404 | 5'-CTATTTTCTATTTTCTATTTTCTATTTTCT TCTGTCCCAGATCCACTGCCACTGAACCTT-3' | 4 |
| 405 | 5'-CTATTTTCTATTTTCTATTTTCTATTTTCT GCAGCCACAGTTCGCTTCATCTGCACCTTG-3' | 5 |
| 406 | 5'-CTATTTTCTATTTTCTATTTTCTATTTTCT TTTCAACTGCTCATCAGATGGCGGGAAGAT-3' | 6 |
| 407 | 5'-CTATTTTCTATTTTCTATTTTCTATTTTCT AAGTTATTCAGCAGGCACACAACAGAGGCA-3' | 7 |
| 408 | 5'-CTATTTTCTATTTTCTATTTTCTATTTTCT GGCGTTATCCACCTTCCACTGTACTTTGGC-3' | 8 |
| 409 | 5'-CTATTTTCTATTTTCTATTTTCTATTTTCT TAGGTGCTGTCCTTGCTGTCCTGCTCTGTG-3' | 9 |
| 410 | 5'-CTATTTTCTATTTTCTATTTTCTATTTTCT GTAGTCTGCTTTGCTCAGCGTCAGGGTGCT-3' | 10 |

TABLE 1-continued

| Probe ID | Sequence | SEQ ID |
|---|---|---|
| 411 | 5'-CTATTTTCTATTTTCTATTTTCTATTTTCT GATGGGTGACTTCGCAGGCGTAGACTTTGT-3' | 11 |
| 412 | 5'-CTATTTTCTATTTTCTATTTTCTATTTTCT CTCTCCCCTGTTGAAGCTCTTTGTGACGGG-3' | 12 |
| 413 | 5'-CTATTTTCTATTTTCTATTTTCTATTTTCT TGGAACTGAGGAGCAGGTGGGGGCACTTCT-3' | 13 |
| 414 | 5'-CTATTTTCTATTTTCTATTTTCTATTTTCT GAAAAAGGGTCAGAGGCCAAAGGATGGGAG-3' | 14 |
| 415 | 5'-CTATTTTCTATTTTCTATTTTCTATTTTCT AGATGAGCTGGAGGACCGCAATAGGGGTAG-3' | 15 |
| 416 | 5'-CTATTTTCTATTTTCTATTTTCTATTTTCT GCATAATTAAAGCCAAGGAGGAGGAGGGGG-3' | 16 |
| 501 | 5'-CTATTTTCTATTTTCTATTTTCTATTTTCT CCTGAGTGAGGAGGGTGAGGAGCAGCAGAG-3' | 17 |
| 502 | 5'-CTATTTTCTATTTTCTATTTTCTATTTTCT AGACCCAGACACGGAGGCAGGCTGAGTCAG-3' | 18 |
| 503 | 5'-CTATTTTCTATTTTCTATTTTCTATTTTCT TGTTGGTTCCAGTGCAGGAGATGGTGATCG-3' | 19 |
| 504 | 5'-CTATTTTCTATTTTCTATTTTCTATTTTCT TAAATCATGATTTTGGGGCTTTGCCTGGG-3' | 20 |
| 505 | 5'-CTATTTTCTATTTTCTATTTTCTATTTTCT TGTTGCCAGACTTGGAGCCAGAGAAGCGAT-3' | 21 |
| 506 | 5'-CTATTTTCTATTTTCTATTTTCTATTTTCT AATAATCAGCCTCGTCCTCAGCCTGGAGCC-3' | 22 |
| 507 | 5'-CTATTTTCTATTTTCTATTTTCTATTTTCT GGTCCCTCCGCCGAAAACCACAGTGTAACT-3' | 23 |
| 508 | 5'-CTATTTTCTATTTTCTATTTTCTATTTTCT TTATGAGACACACCAGTGTGGCCTTGTTGG-3' | 24 |
| 509 | 5'-CTATTTTCTATTTTCTATTTTCTATTTTCT CTGCTCAGGCGTCAGGCTCAGATAGCTGCT-3' | 25 |
| 511 | 5'-CTATTTTCTATTTTCTATTTTCTATTTTCT ATGCGTGACCTGGCAGCTGTAGCTTCTGTG-3' | 26 |
| 512 | 5'-CTATTTTCTATTTTCTATTTTCTATTTTCT ATTCTGTAGGGGCCACTGTCTTCTCCACGG-3' | 27 |
| 513 | 5'-CTATTTTCTATTTTCTATTTTCTATTTTCT CCTCCCCTGGGATCCTGCAGCTCTAGTCTC-3' | 28 |
| 515 | 5'-CTATTTTCTATTTTCTATTTTCTATTTTCT TGAGGGTTTATTGAGTGCAGGGAGAAGGGC-3' | 29 |
| 221 | 5'-CTATTTTCTATTTTCTATTTTCTATTTTCT GGAGGTCAAAACAGCGTGGATGGCG-3' | 30 |
| 222 | 5'-CTATTTTCTATTTTCTATTTTCTATTTTCT GAGGCTGGATCGGTCCCGGTGTCTT-3' | 31 |
| 223 | 5'-CTATTTTCTATTTTCTATTTTCTATTTTCT AATCCGCGTTCCAATGCACCGTTCC-3' | 32 |
| 224 | 5'-CTATTTTCTATTTTCTATTTTCTATTTTCT TAAAAACTGCGGGCACTGGGACGG-3' | 33 |
| 225 | 5'-CTATTTTCTATTTTCTATTTTCTATTTTCT ACCCGAGATTCGCGTGGAGATCCCA-3' | 34 |
| 226 | 5'-CTATTTTCTATTTTCTATTTTCTATTTTCT GAGCAAGGAGCTGCCGAGCGACCAT-3' | 35 |
| 227 | 5'-CTATTTTCTATTTTCTATTTTCTATTTTCT ACACTGGTGGTGGTGGGCATCGTGC-3' | 36 |
| 228 | 5'-CTATTTTCTATTTTCTATTTTCTATTTTCT TTCCAAATGCGTCAGCGGTGCAAGC-3' | 37 |
| 229 | 5'-CTATTTTCTATTTTCTATTTTCTATTTTCT AGCTGCCTGCATCTTCTTCTGCCGC-3' | 38 |
| 230 | 5'-CTATTTTCTATTTTCTATTTTCTATTTTCT CCCTCCACCGTTAACAGCACCGCAA-3' | 39 |
| 231 | 5'-CTATTTTCTATTTTCTATTTTCTATTTTCT TTGGTCACGGGTGTCTCGGGCCTAA-3' | 40 |
| 232 | 5'-CTATTTTCTATTTTCTATTTTCTATTTTCT TCGGCCAACTCTGGAAACAGCGGGT-3' | 41 |
| 233 | 5'-CTATTTTCTATTTTCTATTTTCTATTTTCT TCGGGGTTCTCGTTGCAATCCTCGG-3' | 42 |
| 234 | 5'-CTATTTTCTATTTTCTATTTTCTATTTTCT ATCTCGATGCCCCGCTCACATGCAA-3' | 43 |
| 235 | 5'-CTATTTTCTATTTTCTATTTTCTATTTTCT TGCCGCACCATGTCCACTCGAACCT-3' | 44 |
| 236 | 5'-CTATTTTCTATTTTCTATTTTCTATTTTCT GTTAGCGGCGCCCTTGCTCACATCA-3' | 45 |
| 237 | 5'-CTATTTTCTATTTTCTATTTTCTATTTTCT TGCAGATCTCCTCAATGCGGCGCTT-3' | 46 |
| 238 | 5'-CTATTTTCTATTTTCTATTTTCTATTTTCT TCTCAGAGGATCGGCCCCCAGAATG-3' | 47 |
| 239 | 5'-CTATTTTCTATTTTCTATTTTCTATTTTCT CCTCATCTGACTCCTCGGCGATGGC-3' | 48 |

TABLE 1-continued

| Probe ID | Sequence | SEQ ID |
|---|---|---|
| 240 | 5'-CTATTTTCTATTTTCTATTTTCTATTTTCT CGGGTACAGGGGACTCTGGGGGTGA-3' | 49 |
| 241 | 5'-CTATTTTCTATTTTCTATTTTCTATTTTCT GGGTGGGTGCTCTTGCCTCCAGAGG-3' | 50 |
| 100A2 | 5'-CTATTTTCTATTTTCTATTTTCTATTTTCT GACCTCGGGTCGGTAGCACCGCACT-3' | 51 |
| 100C2 | 5'-CTATTTTCTATTTTCTATTTTCTATTTTCT GGAAGCCTCTCTTCTCCTCCCCGG-3' | 52 |
| 100A1 | 5'-CTATTTTCTATTTTCTATTTTCTATTTTCT CCACAGACACCGTCCTCACCACCCG-3' | 53 |
| 100B1 | 5'-CTATTTTCTATTTTCTATTTTCTATTTTCT GGCTACAGCCACACACGTCTCCTCC-3' | 54 |
| 301 | 5'-CTATTTTCTATTTTCTATTTTCTATTTTCT CGAGGCGGGCGGATCACCTGAGGTC-3' | 55 |
| 302 | 5'-CTATTTTCTATTTTCTATTTTCTATTTTCT CGGGAGGCGGAGGTTGCAGTGAGCC-3' | 56 |
| 320 | 5'-CTATTTTCTATTTTCTATTTTCTATTTTCT TTTTTTTTTTTTTTTTTTTTTTTTT-3' | 57 |
| | 5'-CTATTTTCTATTTTCTATTTTCTATTTTCT-3' | 58 |
| | 5'-CCAGAGTAGC AGGAGCCCCA GGAGCTGAGC-3' | 59 |
| | 5'-GGATGGAGAC TGGGTCAACT GGATGTCACA-3' | 60 |
| | 5'-GCAAGCGATG GTGACTCTGT CTCCTACAGC-3' | 61 |
| | 5'-TCTGTCCCAG ATCCACTGCC ACTGAACCTT-3' | 62 |
| | 5'-GCAGCCACAG TTCGCTTCAT CTGCACCTTG-3' | 63 |
| | 5'-TTTCAACTGC TCATCAGATG GCGGGAAGAT-3' | 64 |
| | 5'-AAGTTATTCA GCAGGCACAC AACAGAGGCA-3' | 65 |
| | 5'-GGCGTTATCC ACCTTCCACT GTACTTTGGC-3' | 66 |
| | 5'-TAGGTGCTGT CCTTGCTGTC CTGCTCTGTG-3' | 67 |
| | 5'-GTAGTCTGCT TTGCTCAGCG TCAGGGTGCT-3' | 68 |
| | 5'-GATGGGTGAC TTCGCAGGCG TAGACTTTGT-3' | 69 |
| | 5'-CTCTCCCCTG TTGAAGCTCT TTGTGACGGG-3' | 70 |
| | 5'-TGGAACTGAG GAGCAGGTGG GGGCACTTCT-3' | 71 |
| | 5'-GAAAAAGGGT CAGAGGCCAA AGGATGGGAG-3' | 72 |
| | 5'-AGATGAGCTG GAGGACCGCA ATAGGGGTAG-3' | 73 |
| | 5'-GCATAATTAA AGCCAAGGAG GAGGAGGGGG-3' | 74 |
| | 5'-CCTGAGTGAG GAGGGTGAGG AGCAGCAGAG-3' | 75 |
| | 5'-AGACCCAGAC ACGGAGGCAG GCTGAGTCAG-3' | 76 |
| | 5'-TGTTGGTTCC AGTGCAGGAG ATGGTGATCG-3' | 77 |
| | 5'-TAAATCATGA TTTTGGGGGC TTTGCCTGGG-3' | 78 |
| | 5'-TGTTGCCAGA CTTGGAGCCA GAGAAGCGAT-3' | 79 |
| | 5'-AATAATCAGC CTCGTCCTCA GCCTGGAGCC-3' | 80 |
| | 5'-GGTCCCTCCG CCGAAAACCA CAGTGTAACT-3' | 81 |
| | 5'-TTATGAGACA CACCAGTGTG GCCTTGTTGG-3' | 82 |
| | 5'-CTGCTCAGGC GTCAGGCTCA GATAGCTGCT-3' | 83 |
| | 5'-ATGCGTGACC TGGCAGCTGT AGCTTCTGTG-3' | 84 |
| | 5'-ATTCTGTAGG GGCCACTGTC TTCTCCACGG-3' | 85 |
| | 5'-CCTCCCCTGG GATCCTGCAG CTCTAGTCTC-3' | 86 |
| | 5'-TGAGGGTTTA TTGAGTGCAG GGAGAAGGGC-3' | 87 |

TABLE 1-continued

| Probe ID | Sequence | SEQ ID |
|---|---|---|
| | 5'-GGAGGTCAAA ACAGCGTGGA TGGCG-3' | 88 |
| | 5'-GAGGCTGGAT CGGTCCCGGT GTCTT-3' | 89 |
| | 5'-AATCCGCGTT CCAATGCACC GTTCC-3' | 90 |
| | 5'-TAAAAACTGC GGGCACTGGG GACGG-3' | 91 |
| | 5'-ACCCGAGATT CGCGTGGAGA TCCCA-3' | 92 |
| | 5'-GAGCAAGGAG CTGCCGAGCG ACCAT-3' | 93 |
| | 5'-ACACTGGTGG TGGTGGGCAT CGTGC-3' | 94 |
| | 5'-TTCCAAATGC GTCAGCGGTG CAAGC-3' | 95 |
| | 5'-AGCTGCCTGC ATCTTCTTCT GCCGC-3' | 96 |
| | 5'-CCCTCCACCG TTAACAGCAC CGCAA-3' | 97 |
| | 5'-TTGGTCACGG GTGTCTCGGG CCTAA-3' | 98 |
| | 5'-TCGGCCAACT CTGGAAACAG CGGGT-3' | 99 |
| | 5'-TCGGGGTTCT CGTTGCAATC CTCGG-3' | 100 |
| | 5'-ATCTCGATGC CCCGCTCACA TGCAA-3' | 101 |
| | 5'-TGCCGCACCA TGTCCACTCG AACCT-3' | 102 |
| | 5'-GTTAGCGGCG CCCTTGCTCA CATCA-3' | 103 |
| | 5'-TGCAGATCTC CTCAATGCGG CGCTT-3' | 104 |
| | 5'-TCTCAGAGGA TCGGCCCCCA GAATG-3' | 105 |
| | 5'-CCTCATCTGA CTCCTCGGCG ATGGC-3' | 106 |
| | 5'-CGGGTACAGG GGACTCTGGG GGTGA-3' | 107 |
| | 5'-GGGTGGGTGC TCTTGCCTCC AGAGG-3' | 108 |
| | 5'-GACCTCGGGT CGGTAGCACC GCACT-3' | 109 |
| | 5'-GGAAGCCTCT CTTCTCCTCC CCCGG-3' | 110 |
| | 5'-CCACAGACAC CGTCCTCACC ACCCG-3' | 111 |
| | 5'-GGCTACAGCC ACACACGTCT CCTCCC-3' | 112 |
| | 5'-CGAGGCGGGC GGATCACCTG AGGTC-3' | 113 |
| | 5'-CGGGAGGCGG AGGTTGCAGT GAGCC-3' | 114 |
| | 5'-TTTTTTTTTT TTTTTTTTTT TTTTTTTTT-3' | 115 |
| 301A | 5'-CTATTTTTCTATTTTTCTTTT CGAGGCGGGCGGATCACCTGAGGTC-3' | 116 |
| 302C | 5'-CTATTTTTCTATTTTTCTTTT CGGGAGGCGGAGGTTGCAGTGAGCC-3' | 117 |
| 302A4 | 5'-CTATTTTATACTTTATATTTCATATTTTATCT CGGGAGGCGGAGGTTGCAGTGAGCC-3' | 118 |
| 302A3/2 | 5'-CTATTTTATATTTATATTTCT CGGGAGGCGGAGGTTGCAGTGAGCC ACTATTTTATACTT-3 | 119 |
| 1002A32 | 5'-CTATTTTATACTTTATATTTCT GACCTCGGGTCGGTAGCACCGCAC TACTATTTTATACTT-3' | 120 |
| 301A2/2 | 5'-CTATTTTTCTT CGAGGCGGGCGGATCACCTGAGGTC TTCTTTTTATCTT-3 | 121 |
| 301A3/2 | 5'-CTATTTTATACTTTATATTTCT CGAGGCGGGCGGATCACCTGAGGTC ACTATTTTATACTT-3' | 122 |

TABLE 2

| Probe ID # | Sequence | SEQ ID # |
|---|---|---|
| | 5'-CTATTTTCTATTTTTCTTTT | 123 |
| | 5'-CTATTTTATACTTTATATTTCATATTTTATCT | 124 |
| 330 | 5'-CTATTTTCTATTTTCTATTTTCTATTTTCT | 58 |
| | 5'-CTATTTTATACTTTATATTTCT..........ACTATTTTATACTT-3 | 125 |
| | 5'-CTATTTTTCTT..........TTCTTTTTATCTT-3 | 126 |

The Sequence Listing is submitted as an ASCII text file in the form of the file named Sequence_Listing.txt, which was created on Oct. 19, 2010, and is 25,342 bytes, which is incorporated by reference herein.

It should be understood that the foregoing disclosure emphasizes certain specific embodiments of the invention and that all modifications or alternatives equivalent thereto are within the spirit and scope of the invention as set forth in the appended claims.

---

We claim:

1. A method for preparing a synthetic oligonucleotide probe, comprising:
   preparing an oligonucleotide molecule, wherein the oligonucleotide molecule comprises:
   a first domain consisting of the sequence 5'-(CTATTTT)$_n$ CT-3', wherein "n" is at least four and the first domain is detectably labeled through at least one cytosine in the sequence; and
   a second domain comprising a target sequence capable of hybridizing to a DNA or RNA sequence, wherein the second domain is not detectably labeled,
   thereby preparing the synthetic oligonucleotide probe.

2. The method of claim 1, wherein the first domain is located 5' of the second domain or the first domain is located 3' of the second domain.

3. The method of claim 1, wherein the first domain is detectably labeled with a reporter molecule or a hapten.

4. The method of claim 3, wherein the hapten is fluorescein linked to the N4 nitrogen of cytosine through an $N_4$-[2,2,-oxy-bis-(ethylamine)]-2'-deoxycytidine-5'-nucleotide linker.

5. The method of claim 3, wherein the reporter molecule is a fluorophore.

6. A method for preparing a synthetic oligonucleotide probe, comprising:
   preparing an oligonucleotide molecule, wherein the oligonucleotide molecule comprises:
   a first domain consisting of the sequence 5'-(CTATTTT)$_n$ CT-3', wherein "n" is at least four and the first domain is detectably labeled through at least one cytosine in the sequence; and
   a second domain comprising a target sequence capable of hybridizing to a DNA or RNA sequence, wherein the second domain is not detectably labeled, and wherein the second domain comprises a sequence selected from the group consisting of SEQ ID NOs: 59-114.

* * * * *